United States Patent
Ono et al.

(10) Patent No.: US 10,238,278 B2
(45) Date of Patent: Mar. 26, 2019

(54) OPHTHALMIC INFORMATION SYSTEM AND OPHTHALMIC INFORMATION PROCESSING SERVER

(71) Applicant: KABUSHIKI KAISHA TOPCON, Itabashi-ku (JP)

(72) Inventors: Yusuke Ono, Kita-ku (JP); Taiki Aimi, Musashino (JP); Masayuki Ito, Itabashi-ku (JP)

(73) Assignee: KABUSHIKI KAISHA TOPCON, Itabashi-ku (JP)

( * ) Notice: Subject to any disclaimer, the term of this patent is extended or adjusted under 35 U.S.C. 154(b) by 21 days.

(21) Appl. No.: 15/302,130

(22) PCT Filed: Mar. 26, 2015

(86) PCT No.: PCT/JP2015/059335
§ 371 (c)(1),
(2) Date: Oct. 5, 2016

(87) PCT Pub. No.: WO2015/156140
PCT Pub. Date: Oct. 15, 2015

(65) Prior Publication Data
US 2017/0188816 A1 Jul. 6, 2017

(30) Foreign Application Priority Data
Apr. 7, 2014 (JP) ................. 2014-078543

(51) Int. Cl.
*A61B 3/00* (2006.01)
*G06F 19/00* (2018.01)
(Continued)

(52) U.S. Cl.
CPC ............ *A61B 3/0033* (2013.01); *A61B 3/102* (2013.01); *A61B 3/18* (2013.01); *G06F 19/00* (2013.01);
(Continued)

(58) Field of Classification Search
CPC ....... A61B 3/10; A61B 3/0066; A61B 3/0033; A61B 3/102; A61B 3/18; G06F 19/30;
(Continued)

(56) References Cited

U.S. PATENT DOCUMENTS 6,377,349 B1  4/2002  Fercher
2003/0074221 A1*  4/2003  Christ ................. G06F 19/3418
705/2
(Continued)

FOREIGN PATENT DOCUMENTS

JP  11-85875 A  3/1999
JP  11-325849 A  11/1999
(Continued)

OTHER PUBLICATIONS

International Search Report dated Jun. 30, 2015 in PCT/JP15/059335 Filed Mar. 26, 2015.
(Continued)

*Primary Examiner* — Jordan Schwartz
(74) *Attorney, Agent, or Firm* — Oblon, McClelland, Maier & Neustadt, L.L.P.

(57) ABSTRACT

An ophthalmic information system for long-term management of pathological conditions, in which, upon receipt of patient identification information and examination data from an ophthalmic examination apparatus, a server of the system specifies a medical institution terminal corresponding to the patient identification information, and sends the patient identification information and the examination data received to the medical institution terminal specified. Further, upon receipt of the patient identification information and a report based on the examination data from the medical institution terminal, the server stores at least part of the report in a patient information storage area associated with the patient identification information, and sends at least part of the
(Continued)

report to a patient terminal corresponding to the patient identification information.

14 Claims, 11 Drawing Sheets

(51) Int. Cl.
*G16H 10/60* (2018.01)
*G16H 80/00* (2018.01)
*A61B 3/10* (2006.01)
*A61B 3/18* (2006.01)
*G06Q 50/24* (2012.01)

(52) U.S. Cl.
CPC ........ *G06F 19/321* (2013.01); *G06F 19/3418* (2013.01); *G06Q 50/24* (2013.01); *G16H 10/60* (2018.01); *G16H 80/00* (2018.01); *G06F 19/34* (2013.01)

(58) Field of Classification Search
CPC ...... G06F 19/32; G06F 19/3425; G06F 19/34; G06F 19/321; G06F 19/3418; G06F 19/322; G16H 10/00; G16H 10/60; G16H 15/00; G06Q 50/24
See application file for complete search history.

(56) References Cited

U.S. PATENT DOCUMENTS

| | | | |
|---|---|---|---|
| 2006/0100528 A1 | 5/2006 | Chan et al. | |
| 2007/0162305 A1* | 7/2007 | Miller | G06Q 10/00 705/2 |
| 2007/0222945 A1* | 9/2007 | Tsukada | A61B 3/102 351/205 |
| 2007/0285619 A1 | 12/2007 | Aoki et al. | |
| 2008/0204655 A1 | 8/2008 | Kikawa et al. | |
| 2009/0244485 A1 | 10/2009 | Walsh et al. | |
| 2010/0189334 A1 | 7/2010 | Tomidokoro et al. | |
| 2010/0194757 A1 | 8/2010 | Tomidokoro et al. | |
| 2013/0201449 A1 | 8/2013 | Walsh et al. | |
| 2014/0129259 A1* | 5/2014 | Seriani | G06F 19/3418 705/3 |
| 2015/0042951 A1* | 2/2015 | Stanga | A61B 3/0025 351/206 |
| 2015/0085252 A1 | 3/2015 | Fujimura et al. | |
| 2015/0138503 A1 | 5/2015 | Walsh et al. | |
| 2016/0071225 A1* | 3/2016 | Chmait | G06Q 20/102 705/2 |
| 2016/0183796 A1* | 6/2016 | Fukuma | G06F 19/3418 705/2 |

FOREIGN PATENT DOCUMENTS

| | | | |
|---|---|---|---|
| JP | 2002-238858 | * | 8/2002 |
| JP | 2002-238858 A | | 8/2002 |
| JP | 2003-167955 A | | 6/2003 |
| JP | 2004-199631 A | | 7/2004 |
| JP | 2005-285033 A | | 10/2005 |
| JP | 2006-153838 A | | 6/2006 |
| JP | 2007-24677 A | | 2/2007 |
| JP | 2007-325831 A | | 12/2007 |
| JP | 2008-158622 A | | 7/2008 |
| JP | 2008-206684 A | | 9/2008 |
| JP | 2009-20794 A | | 1/2009 |
| JP | 2009-61203 A | | 3/2009 |
| JP | 2009-66015 A | | 4/2009 |
| JP | 2011-515194 A | | 5/2011 |
| JP | 2013-248376 A | | 12/2013 |

OTHER PUBLICATIONS

Japanese Office Action dated Dec. 12, 2017 in Patent Application No. 2014-078543 (with English translation), citing document AX therein, 6 pages.
Office Action dated Sep. 26, 2017 in Japanese Patent Application No. 2014-078543.

* cited by examiner

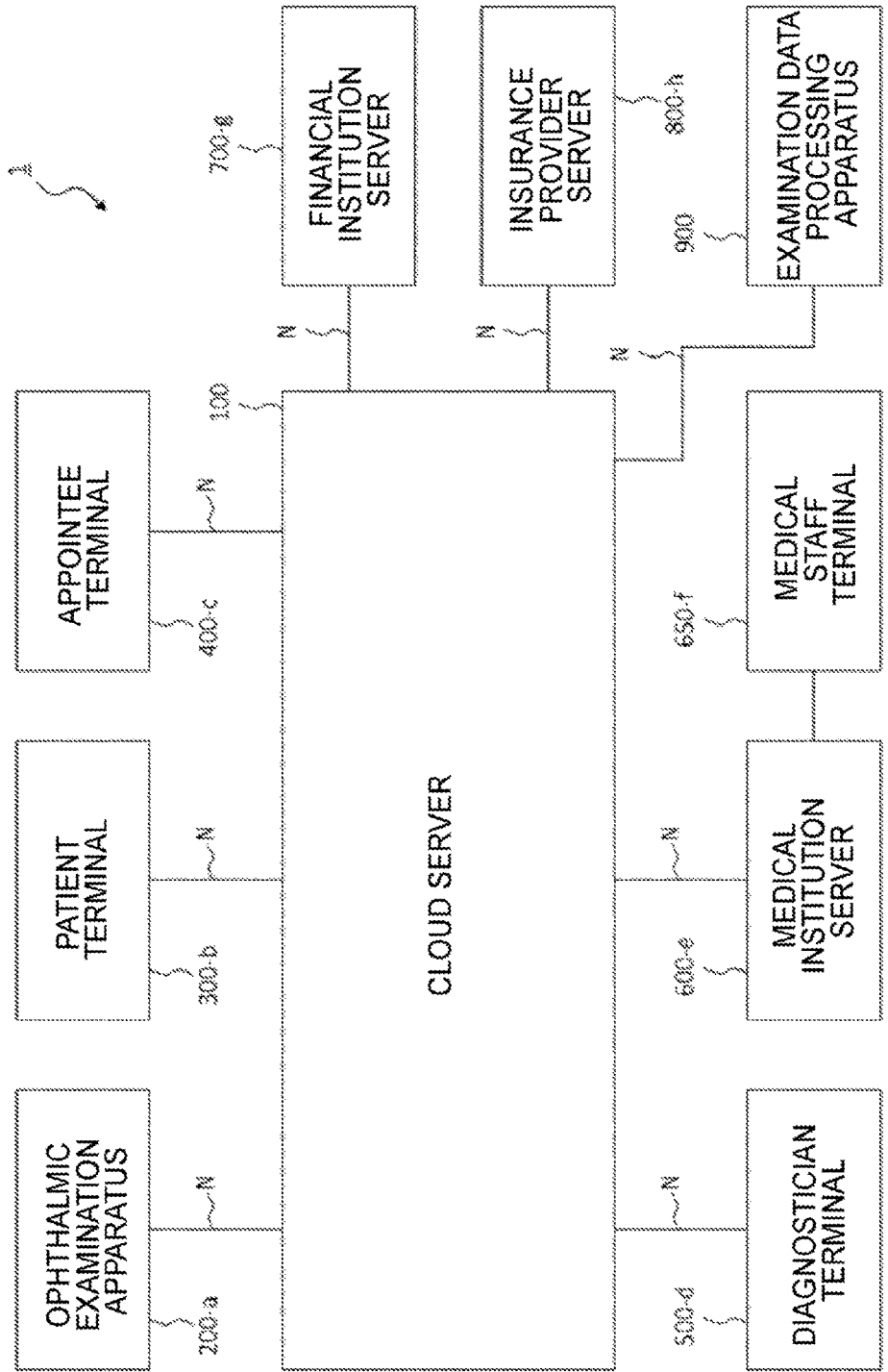

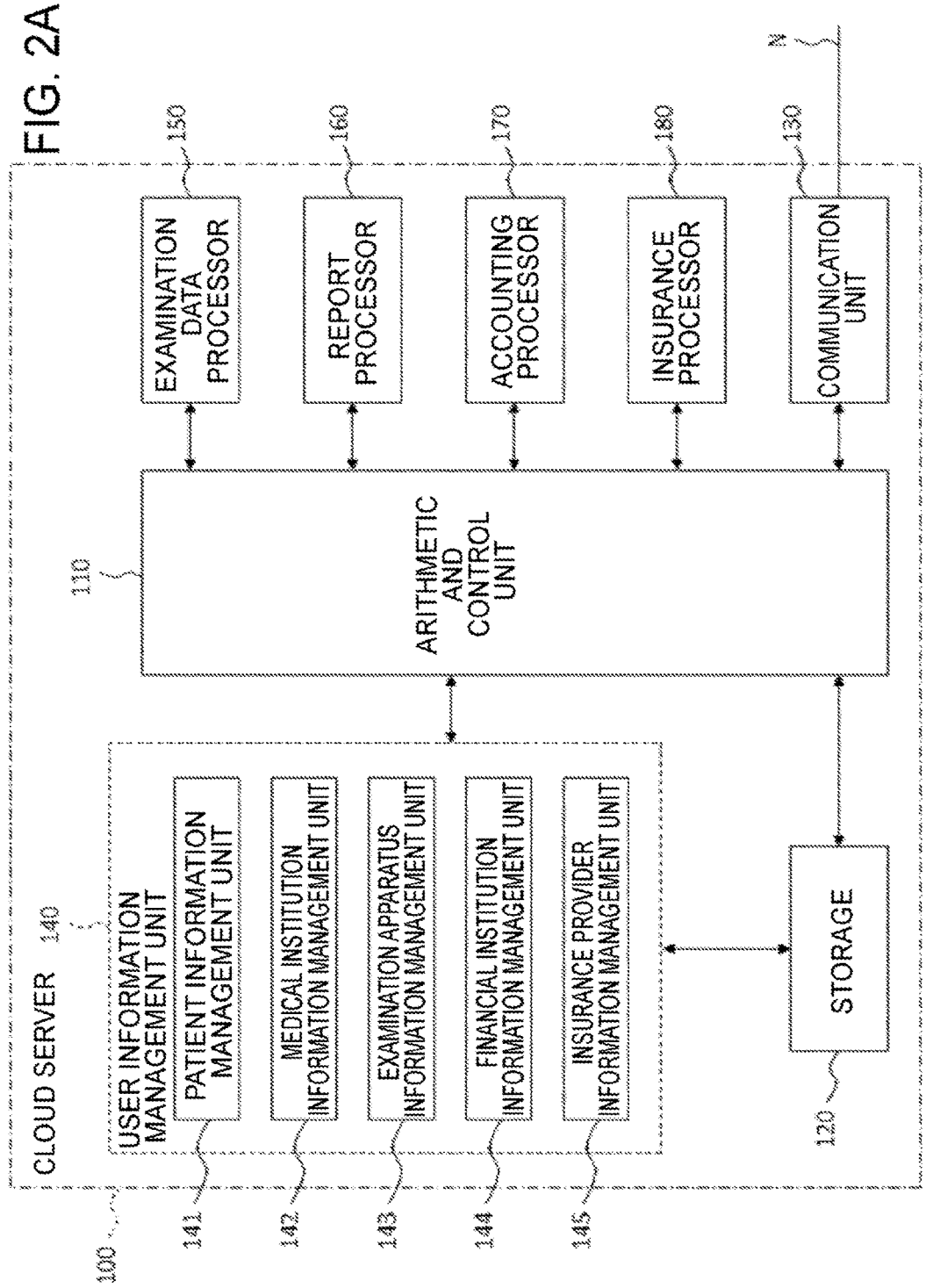

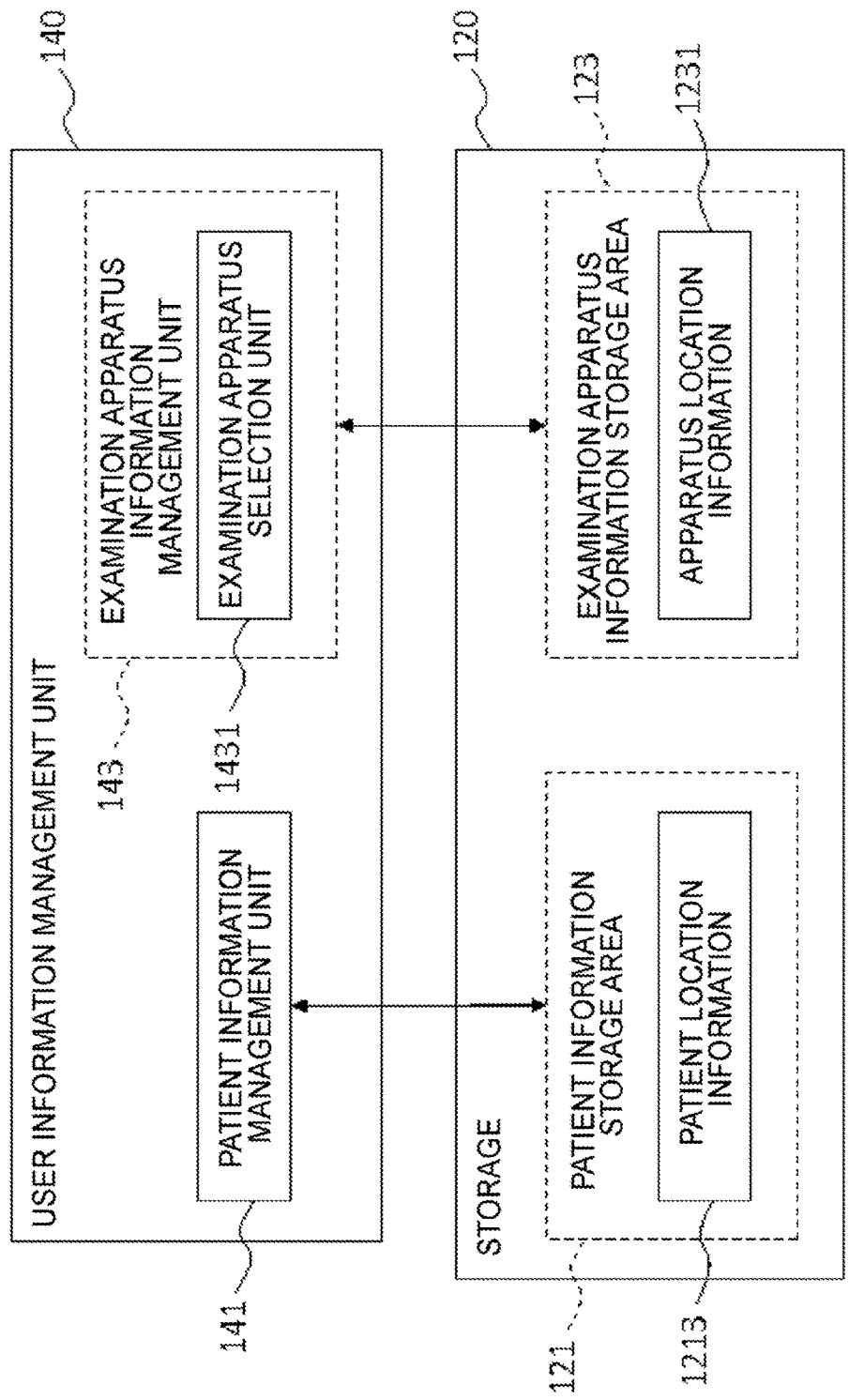

OPHTHALMIC INFORMATION SYSTEM AND OPHTHALMIC INFORMATION PROCESSING SERVER

Embodiments described herein relate generally to a system and a server for processing ophthalmic information.

Home care is one of medical approaches to a patient in need of long-term care. Home care is provided to a patient in a location other than medical institutions (e.g., home, elderly welfare facilities, etc. collectively referred to as "home or the like"). For providing a home care, a medical device is installed in a home or the like, and the medical device is remotely managed (see, for example, patent documents 1 to 3).

With the progress of recent aging society, home care is expected to be more common. It is also expected that factors such as aging and changes in the lifestyle cause an increase in ophthalmic diseases including age-related macular degeneration, diabetic retinopathy, glaucoma, and the like. These ophthalmic diseases may lead to blindness, and requires long-term management.

However, it is difficult to manage such ophthalmic diseases by conventional home care technology. More specifically, the management of these ophthalmic diseases requires understanding the pathological conditions. To accurately understand the pathological conditions, in addition to a subjective test using a visual target, another test has to be performed to figure out the structure, properties and the like of the eye.

Examples of devices used to figure out the structure of the eye include the following:

Optical coherence tomography (OCT) apparatus for capturing sectional images of the fundus, the cornea, and the like using OCT;

Fundus camera for capturing images of the fundus; and

Scanning laser ophthalmoscope (SLO) for capturing images of the fundus by laser scanning using a confocal optical system.

Besides, examples of devices used to figure out the properties of the eye include the following:

Eye refraction test device for measuring the refractive properties of the eye (refractometer, keratometer);

Tonometer for measuring the intraocular pressure; Specular microscope for obtaining the properties of the cornea (corneal thickness, distribution of cells, etc.); and Wavefront analyzer for acquiring information on the aberration of the eye using a Hartmann-Shack sensor.

In this way, a variety of test devices are used in the ophthalmic field. Especially, the OCT device is increasingly attracting attention in recent years. This is because the remarkable advantage of the OCT device that it is capable of capturing high-resolution images as well as sectional images and three-dimensional images. As described below, there are various OCT systems.

Patent Document 4 discloses a device using Fourier-domain OCT or frequency-domain OCT. This device scans an object to be measured with a low-coherence light beam, and superposes the light reflected from the object on reference light to generate interference light. The device then obtains the spectral intensity distribution of the interference light by using a spectrometer, and applies Fourier transform to the spectral intensity distribution to acquire an image of a scanned cross-section. Such technique using a spectrometer is called "spectral-domain".

Patent Document 5 discloses a device using swept-source OCT, i.e., a type of Fourier-domain OCT. This device varies (sweeps) the wavelengths of light irradiated to the object to be measured, and sequentially detects interference light obtained by superposing reflected light of each wavelength on reference light to acquire spectral intensity distribution. The device applies Fourier transform to the spectral intensity distribution to form an image.

Patent Document 6 discloses a device using full-field OCT or en-face OCT. This device irradiates light beams having a predetermined diameter to an object to be measured, and analyzes the components of interference light obtained by superposing the reflected light on reference light. Thereby, the device captures an image of a cross-section perpendicular to the traveling direction of the light.

Patent Document 7 discloses a configuration in which OCT is applied to the ophthalmic field. Patent Document 8 discloses an ophthalmic examination apparatus obtained by combining an OCT device and a subjective visual acuity test system, for providing diagnostic materials for the maculopathy and the glaucoma.

[Patent Document 1] Japanese Unexamined Patent Application Publication No. 2009-20794

[Patent Document 2] Japanese Unexamined Patent Application Publication No. 2005-285033

[Patent Document 3] Japanese Unexamined Patent Application Publication No. 2004-199631

[Patent Document 4] Japanese Unexamined Patent Application Publication No. Hei 11-325849

[Patent Document 5] Japanese Unexamined Patent Application Publication No. 2007-24677

[Patent Document 6] Japanese Unexamined Patent Application Publication No. 2006-153838

[Patent Document 7] Japanese Unexamined Patent Application Publication No. 2013-248376

[Patent Document 8] Japanese Unexamined Patent Application Publication (Translation of PCT Application) No. 2011-515194

As described above, the ophthalmic apparatus such as OCT apparatus is useful to understand the pathological conditions. It is desirable to install the ophthalmic apparatus at home or the like of each patient so that examination can be readily carried out on a regular basis. For that purpose, there are various problems to be solved such as, for example, cost burden on the patient and learning of the operation of the ophthalmic apparatus.

An object of the present invention is to provide a new technology for long-term management of pathological conditions.

According to an exemplary embodiment, an ophthalmic information system includes: a server; a plurality of medical institution terminals installed in a plurality of medical institutions, each of the medical institution terminals being communicable with the server via a communication line; a plurality of ophthalmic examination apparatuses, each communicable with the server via the communication line; and a plurality of patient terminals used by a plurality of patients or those related to the patients, each of the patient terminals being communicable with the server via the communication line.

Each of the plurality of ophthalmic examination apparatuses is installed in a facility different from the plurality of medical institutions, and includes: a first communication unit for communication via the communication line; a receiving unit configured to receive patient identification information; an examination unit configured to generate examination data by optically examining an eye; and a first controller configured to associate the patient identification information received by the receiving unit with the examination data generated by the examination unit, and control the first communication unit to send the patient identification information and the examination data associated with each other to the server.

Each of the plurality of medical institution terminals includes: a second communication unit for communication via the communication line; a user interface used to create a report based on the examination data; and a second controller configured to control the second communication unit to send the report created to the server.

The server includes: a third communication unit for communication via the communication line; a storage including a plurality of patient information storage areas respectively associated with a plurality of patient identification information of the plurality of patients, and storing, in advance, first association information in which each of the plurality of patient identification information is associated with medical institution identification information of one or more of the medical institutions; a data processor configured to, when the third communication unit receives patient identification information and examination data from one of the plurality of ophthalmic examination apparatuses, specify a medical institution terminal corresponding to the patient identification information with reference to the first association information; and a third controller configured to control the third communication unit to send the patient identification information and the examination data received to the medical institution terminal specified by the data processor, wherein, when the third communication unit receives patient identification information and a report from one of the plurality of medical institution terminals, the third controller stores at least part of the report in a patient information storage area associated with the patient identification information, and controls the third communication unit to send at least part of the report to a patient terminal corresponding to the patient identification information.

According to the embodiment, it is possible to provide a new technology for long-term management of pathological conditions.

FIG. 1 is a schematic diagram illustrating an example of the configuration of a system according to an embodiment.

FIG. 2A is a schematic diagram illustrating an example of the configuration of a cloud server according to an embodiment.

FIG. 8A is a schematic diagram illustrating an example of the configuration of a cloud server according to an embodiment.

Figure 2B:
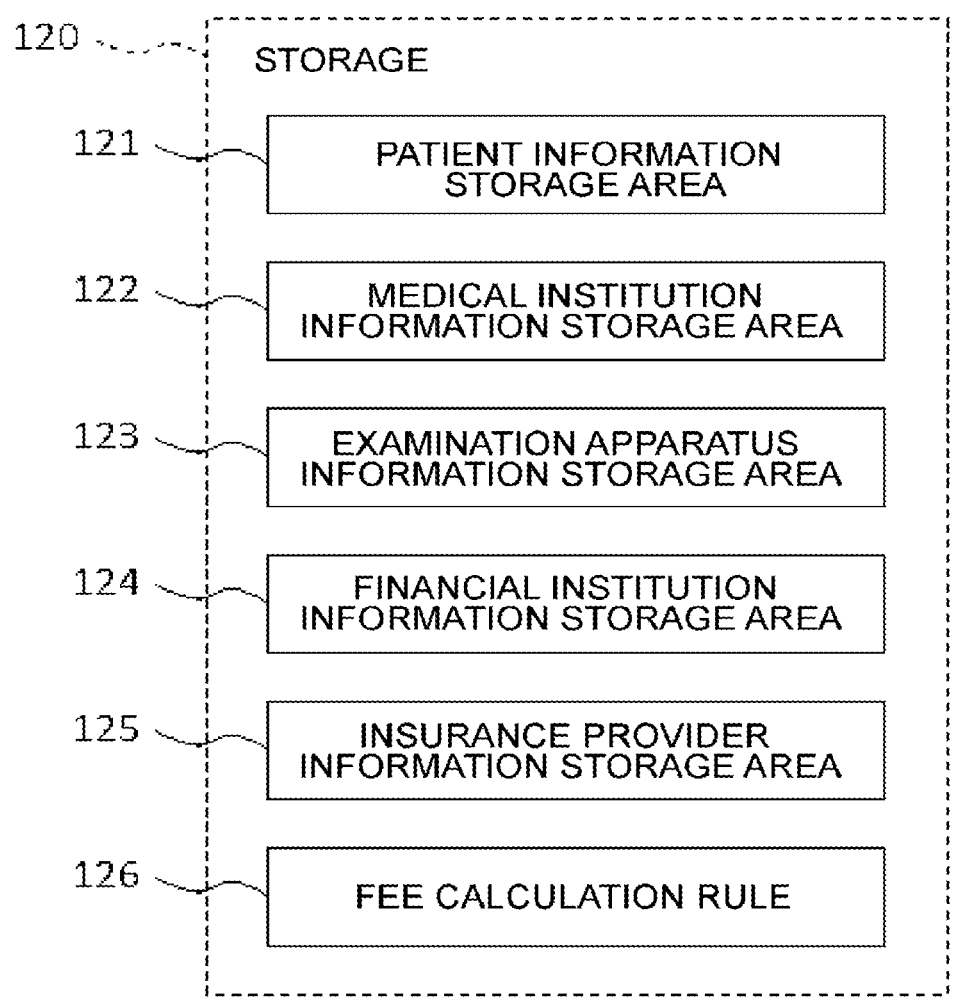
FIG. 2B is a schematic diagram illustrating an example of the configuration of a cloud server according to an embodiment.

Exemplary embodiments of the present invention are described below. Incidentally, the contents of documents cited herein may be incorporated by reference in the following embodiments.

An ophthalmic information system according to an embodiment includes a cloud server as the center of the system. The cloud server provides services to various kinds of computers connectable thereto via a communication line.

[System Configuration]

As illustrated in FIG. 1, an ophthalmic information system 1 may include at least one cloud server 100, a plurality of ophthalmic examination apparatuses 200-$a$ ($a$=1, 2, 3, . . . ), a plurality of patient terminals 300-$b$ ($b$=1, 2, 3, . . . ), a plurality of appointee terminals 400-$c$ ($c$=1, 2, 3, . . . ), a plurality of diagnostician terminals 500-$d$ ($d$=1, 2, 3, . . . ), a plurality of medical institution servers 600-$e$ ($e$=1, 2, 3, . . . ), a plurality of medical staff terminals 650-$f$ ($f$=1, 2, 3, . . . ), a plurality of financial institution servers 700-$g$ ($g$=1, 2, 3, . . . ), a plurality of insurance provider servers 800-$h$ ($h$=1, 2, 3, . . . ), and at least one examination data processing apparatus 900.

In general, the system of the embodiment need not necessarily include all of these information processing apparatuses. It is sufficient if the system is provided with one or more information processing apparatuses for implementing a predetermined function. Besides, one or more new information processing apparatuses can be added to the system along with the functional enhancement.

These information processing apparatuses are connected via a communication line N. The communication line N may include a wide area network (WAN) such as the Internet, a virtual private network, and a dedicated communication line. Further, the communication line N may include a wired communication network and/or a wireless communication network. Note that the communication line between the medical institution server 600-$e$ and the medical staff terminal 650-$f$, that can access the medical institution server 600-$e$, may include a local area network (LAN).

[Cloud Server 100]

The cloud server 100 is described below. The cloud server 100 is a server used for so-called cloud computing, and provides services such as data storage and data processing by means of a computer to a plurality of computers via the communication line N. In this example, the cloud server 100 is capable of providing the services to the ophthalmic examination apparatuses 200-$a$, the patient terminals 300-$b$, the appointee terminals 400-$c$, the diagnostician terminals 500-$d$, the medical institution servers 600-$e$, the financial institution servers 700-$g$, the insurance provider servers 800-$h$, and the examination data processing apparatus 900.

The cloud server 100 includes a microprocessor, random access memory (RAM), read only memory (ROM), a hard disk drive, and the like. The ROM and the hard disk drive store computer programs and data for performing a variety of control and arithmetic processing. By the cooperation of hardware such as the microprocessor and software such as the computer programs, various types of processing can be performed.

FIGS. 2A and 2B each illustrate an example of the internal configuration of the cloud server 100. The cloud server 100 of this embodiment includes an arithmetic and control unit 110, a storage 120, a communication unit 130, a user information management unit 140, an examination data processor 150, a report processor 160, an accounting processor 170, and an insurance processor 180.

(Arithmetic and Control Unit 110)

The arithmetic and control unit 110 controls each unit of the cloud server 100, and performs various types of arithmetic processing. Specific examples of the processing performed by the arithmetic and control unit 110 are described later.

(Storage 120)

The storage 120 stores various types of data. The storage 120 stores information related to the services provided by the cloud server 100. The receivers of the services, that is, the users of the services, include patients, those related to the patients (family members and the like), institutions where an ophthalmic examination apparatus is installed (examination apparatus installation institutions), medical institutions, financial institutions, insurance providers, and the like. Examples of the examination apparatus installation institutions include pharmacies, optician's stores, optometrists, and welfare facilities for the aged. To store information related to such kinds of users, a patient information storage area 121, a medical institution information storage area 122, an examination apparatus information storage area 123, a financial institution information storage area 124, and an insurance provider information storage area 125 are provided in the storage 120.

The patient information storage area 121 is provided for each patient user. In the patient information storage area 121, information related to a corresponding patient user is stored. Examples of the information related to the patient user include user ID (identifier) in the system, authentication information (password, biometrics authentication information, etc.), name, sex, date of birth, contact information (address, phone number, e-mail address, IP address, etc.), information related to accounting, identification information of the relevant medical institution, identification information of the patient user in the medical institution (patient ID), medical information (information acquired by the ophthalmic examination apparatus 200-$a$, analysis result of the information acquired, diagnostic report written by a doctor, part of electronic medical record information, examination history, etc.), identification information of the relevant financial institution, identification information of the patient user in the financial institution, identification information of the relevant insurance provider, identification information of the patient user (insured ID, etc.) in the insurance provider, and the like.

The patient information storage area 121 also stores information on a user (relevant user) related to the patient user. Examples of the information related to the relevant user, authentication information (password, etc.), name, relationship with the patient, contact information (address, phone number, e-mail address, IP address, etc.), information related to accounting, and the like.

The medical institution information storage area 122 is provided for each medical institution user. In the medical institution information storage area 122, information related to the medical institution user is stored. Examples of the information related to the medical institution user include user ID in the system, authentication information (password, etc.), the type of the medical institution (hospital, clinic, medical examination center, etc.), the name of the medical institution, the names of diagnosis and treatment departments, information about the relevant medical personnel (the name of a doctor, disease names that he/she specializes in, etc.), contact information (address, phone number, e-mail address, IP address, etc.), a list of relevant medical institution, identification information of the patient users involved, information about accounting, and the like.

In the examination apparatus information storage area 123, information related to the ophthalmic examination apparatus 200-$a$ is stored. Examples of the information related to the ophthalmic examination apparatus 200-$a$ include identification information of the apparatus (apparatus ID), the type of the institution where the apparatus is installed (a pharmacy, an optician's store, an optometrist, a welfare facility for the aged, etc.), contact information (address, phone number, e-mail address, IP address, the name of a person in charge, etc.), information related to the maintenance, history of examinations performed by the apparatus (the number, frequency, or the like of examination, etc.), and the like. Incidentally, the examination apparatus information storage area 123 may be provided for each of the ophthalmic examination apparatuses 200-$a$, or may be provided for each examination apparatus installation institution.

The financial institution information storage area 124 is provided for each financial institution user. In the financial institution information storage area 124, information related to the financial institution user is stored. Examples of the information related to the financial institution user include user ID in the system, authentication information (password, etc.), the type of the financial institution (bank, credit card company, etc.), the name of the financial institution, contact information (address, phone number, e-mail address, IP address, etc.), user ID, patient ID, or the like of the patient user involved, information about accounting, and the like.

The insurance provider information storage area 125 is provided for each insurance provider user. In the insurance provider information storage area 125, information related to the insurance provider user is stored. Examples of the information related to the insurance provider user include user ID in the system, authentication information (password, etc.), the type of the insurance provider (public insurance, private insurance, etc.), the name of the insurance provider, contact information (address, phone number, e-mail address, IP address, etc.), user ID, patient ID, or the like of the patient involved, and information about accounting.

The storage 120 also stores information other than those described above. Examples of such information include fee calculation rule 126. The fee calculation rule 126 is referred to for the calculation of fees to be levied on various types of users based on the use fee of the system. The fee calculation rule 126 may be provided for each type of the system use fee (the type of accounting). For example, the system use fee occurs each time examination is carried out using the ophthalmic examination apparatus 200-$a$ (the type of accounting), and is charged to the patient user or the insurance provider. The fee based on the system use fee occurs, for example, for the institution where the ophthalmic examination apparatus 200-$a$ used for examination is installed, the medical institution (doctor) that has made a diagnosis based on information (examination data) obtained by the examination, the administering authority of the system (system administering authority), or the like. The fee calculation rule 126 is created in advance based on such accounting structure, fee structure, or the like.

Regarding each round of examination using the ophthalmic examination apparatus 200-$a$, for example, the fee calculation rule 126 records the following information: a fee to be charged is "X"; a fee for the examination apparatus installation institution is "Y1"; a fee for the medical institution is "Y2"; and a fee for the system administering authority is "Y3". Here, X may be represented as follows:

X=Y1+Y2+Y3. However, it is not so limited if taxes or the like are involved. In addition, a fee for some institution(s) may be zero.

Besides, the fee calculation rule 126 may contain information related to various kinds of optional services. For example, the fee to be charged for predetermined analysis on examination data, a fee for the medical institution (doctor) that has made a diagnosis based on the analysis result, and the institution that has conducted the analysis (e.g., system administering authority) may be recorded in the fee calculation rule 126. Incidentally, the optional services are not limited to such analysis, and, for example, may include request, provision, etc. for second opinion, and the like.

Information stored in the storage 120 is not limited to those described above. Other information that may be stored in the storage 120 is described below.

(Communication Unit 130)

The communication unit 130 communicates data with other information processing apparatuses through the communication line N. The data communication method (data communication system) may be arbitrarily selected. The communication unit 130 includes, for example, a communication interface conforming to the Internet, a communication interface conforming to LAN, a communication interface conforming to near field communication, and the like. Data that the communication unit 130 sends and receives may be encrypted. In this case, the arithmetic and control unit 110 includes an encryption processor that encrypts data to be transmitted and a decoder that decodes data received.

(User Information Management Unit 140)

The user information management unit 140 performs processing on information about the users of the system. As described above, the users of the system include patients, those related to the patients, medical institutions, financial institutions, insurance providers, and the like. The user information management unit 140 has functions corresponding to the types of the users of the system. In this embodiment, the user information management unit 140 is provided with a patient information management unit 141, a medical institution information management unit 142, an examination apparatus information management unit 143, a financial institution information management unit 144, and an insurance provider information management unit 145.

(Patient Information Management Unit 141)

The patient information management unit 141 manages the account of each patient user who uses the system. The account of each patient user is associated with a storage area for the patient user provided in the patient information storage area 121. The account is identified by, for example, a user ID assigned to the patient user. Specific examples of processing performed by the patient information management unit 141 are described later.

The patient information management unit 141 performs the authentication of patient users. As described above, a user ID is assigned to each user of the system. In particular, a patient user ID is assigned to each patient user when, for example, he/she starts using the system (at the time of user registration). The patient user is registered, for example, after the determination of diagnosis of a disease treated by the system. The patient user ID is issued, for example, when the patient information management unit 141 receives an input of patient information or the like.

Described below is an example of patient user authentication process. Incidentally, authentication of users of other types can be performed in a similar manner. As described above, the user ID and user authentication information of each user is stored in the patient information storage area 121 of the storage 120.

A user of the ophthalmic examination apparatus 200-*a* enters his/her user ID and user authentication information to the ophthalmic examination apparatus 200-*a* or a device connected thereto. Having performed an examination, the ophthalmic examination apparatus 200-*a* associates acquired examination data with the input user ID and user authentication information, and sends them to the cloud server 100. Incidentally, when a person who is not an authorized patient user uses the ophthalmic examination apparatus 200-*a*, or the like, there are cases in which character string information similar to the user ID, or the like and/or character string information similar to the user authentication information, or the like are/is sent to the cloud server 100.

The patient information management unit 141 checks a combination of the user ID (or character string information similar to it, or the like) and the user authentication information (or character string information similar to it, or the like) sent from the ophthalmic examination apparatus 200-*a* against (each) combination of a user ID and user authentication information stored in the patient information storage area 121. That is, the patient information management unit 141 searches the patient information storage area 121 for a combination of a user ID and user authentication information that matches the combination of the user ID and the user authentication information sent from the ophthalmic examination apparatus 200-*a*.

Having found the combination of interest, the patient information management unit 141 determines that the person having used the ophthalmic examination apparatus 200-*a* is a user of the system. On the other hand, if the combination of interest is not found, the patient information management unit 141 determines that the person having used the ophthalmic examination apparatus 200-*a* is not a user of the system. The cloud server 100 performs predetermined processing corresponding to the determination result.

Incidentally, the ophthalmic examination apparatus 200-*a* may have an authentication function. In this case, the ophthalmic examination apparatus 200-*a* performs the same patient user authentication process as that of the patient information management unit 141. If the authentication is successful, the ophthalmic examination apparatus 200-*a* associates acquired examination data with the input user ID, and sends them to the cloud server 100. On the other hand, if the authentication fails, for example, the ophthalmic examination apparatus 200-*a* prompts the user to re-enter the user ID and user authentication information and performs the patient user authentication process again.

The authentication process may be performed through real time communication between the ophthalmic examination apparatus 200-*a* and the cloud server 100 at the time of examination using the apparatus 200-*a*. Having received an input of a user ID and user authentication information, the ophthalmic examination apparatus 200-*a* sends them to the cloud server 100. The patient information management unit 141 performs the patient user authentication process in the manner described above, and sends the result (success or failure of the authentication) to the ophthalmic examination apparatus 200-*a*. If the authentication is successful, the ophthalmic examination apparatus 200-*a* allows the implementation of the examination, and associates examination data obtained thereby with the user ID, and sends them to the cloud server 100. On the other hand, if the authentication fails, for example, the ophthalmic examination apparatus 200-*a* prompts the user to re-enter the user ID and user authentication information. Then, the same patient user authentication process is performed again.

(Medical Institution Information Management Unit 142)

The medical institution information management unit 142 manages information about medical institution users who use the system by, for example, providing an account for each of the medical institution users. The account of each medical institution user is associated with a storage area for the medical institution user in the medical institution information storage area 122. The account is identified by, for example, a user ID assigned to the medical institution user. Specific examples of processing performed by the medical institution information management unit 142 are described later.

(Examination Apparatus Information Management Unit 143)

The examination apparatus information management unit 143 manages information about each of the ophthalmic examination apparatuses 200-*a* by, for example, providing an account for the ophthalmic examination apparatus 200-*a* (or an account for each examination apparatus installation institution). The account of each of the ophthalmic examination apparatuses 200-*a* (or each examination apparatus installation institution) is associated with a storage area for the ophthalmic examination apparatus 200-*a* (or the examination apparatus installation institution) in the examination apparatus information storage area 123. The account is identified by, for example, the apparatus ID assigned to the ophthalmic examination apparatus 200-*a*, the ID of the examination apparatus installation institution, or the like. Specific examples of processing performed by the examination apparatus information management unit 143 are described later.

(Financial Institution Information Management Unit 144)

The financial institution information management unit 144 manages information about financial institution users who use the system by, for example, providing an account for each of the financial institution users. The account of each financial institution user is associated with a storage area for the financial institution user in the financial institution information storage area 124. The account is identified by, for example, a user ID assigned to the financial institution user. Specific examples of processing performed by the financial institution information management unit 144 are described later.

(Insurance Provider Information Management Unit 145)

The insurance provider information management unit 145 manages information about insurance provider users who use the system by, for example, providing an account for each of the insurance provider users. The account of each insurance provider user is associated with a storage area for the insurance provider user in the insurance provider information storage area 125. The account is identified by, for example, a user ID assigned to the insurance provider user. Specific examples of processing performed by the insurance provider information management unit 145 are described later.

(Examination Data Processor 150)

The ophthalmic information system 1 has a function of processing examination data of the subject's eye E obtained by the ophthalmic examination apparatus 200-*a*. This process may include analysis of examination data. In this embodiment, the cloud server 100 (the examination data processor 150) and the examination data processing apparatus 900 perform the analysis. Incidentally, the analysis performed by the cloud server 100 and that performed by the examination data processing apparatus 900 may include the same process, or the two may be entirely different. For example, the examination data processing apparatus 900 may be configured to perform advanced analysis, while the cloud server 100 may be configured to perform other analysis. In addition, there may be a difference in accounting methods between the analysis performed by the cloud server 100 and that performed by the examination data processing apparatus 900. For example, no charge may be required for the analysis of the cloud server 100 (i.e., the charge is included in the examination fee by using the ophthalmic examination apparatus 200-*a*), and the analysis performed by the examination data processing apparatus 900 may occur an optional fee. In the following, a description is given of examples of analysis that can be performed by the examination data processor 150 and/or the examination data processing apparatus 900.

Figure 3:
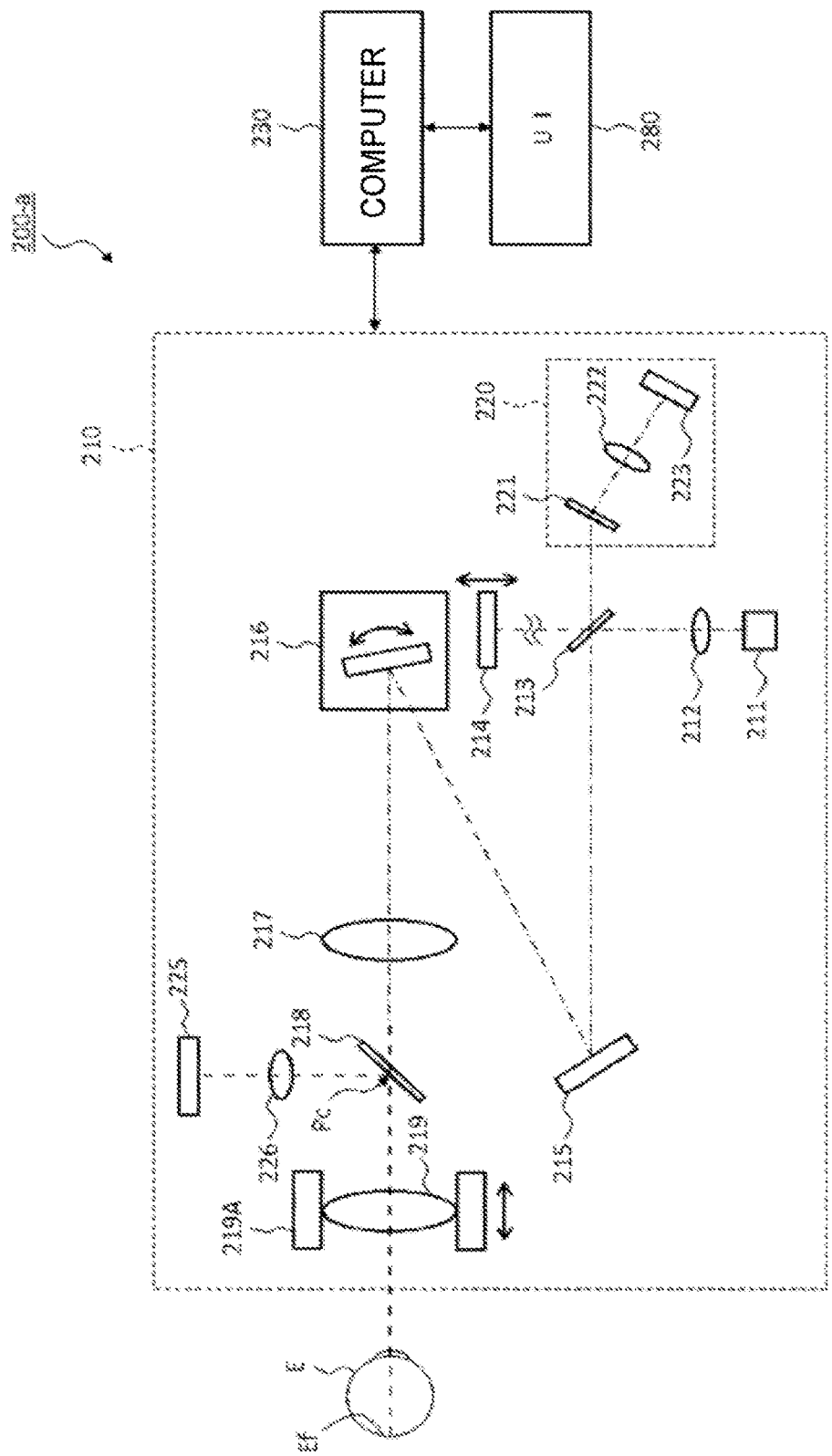
FIG. 3 is a schematic diagram illustrating an example of the configuration of an ophthalmic examination apparatus according to an embodiment.
Figure 4:
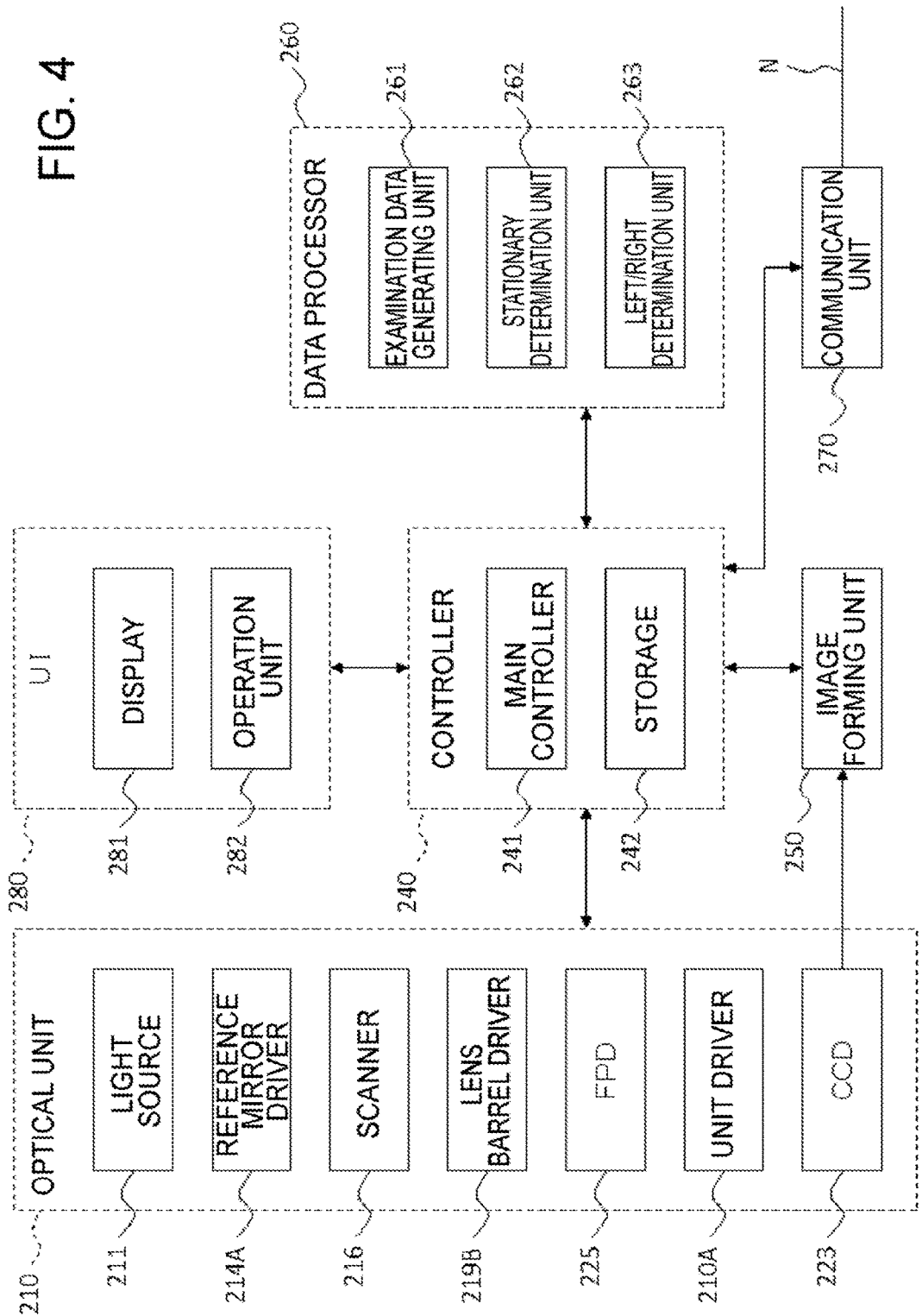
FIG. 4 is a schematic diagram illustrating an example of the configuration of an ophthalmic examination apparatus according to an embodiment.

The examination data processor 150 (or the examination data processing apparatus 900, the same applies hereinafter) performs processing on data (examination data) received from the ophthalmic examination apparatuses 200-*a*. Examples of the examination data include the following:

(1) Signals output from a CCD image sensor 223 illustrated in FIG. 3 or the like (2) Image data generated by an image forming unit 250 illustrated in FIG. 4

(3) Data obtained in the middle of processing performed by the image forming unit 250 (i.e., data obtained in the middle of an image data forming process)

(4) Data obtained by processing signals output from the CCD image sensor 223 by means of a component other than the image forming unit 250

When the ophthalmic examination apparatus 200-*a* has a function of forming image data, i.e., when the image forming unit 250 is included in the ophthalmic examination apparatus 200-*a*, for example, any of the above examination data (1) to (4) is input to the cloud server 100. Meanwhile, when the ophthalmic examination apparatus 200-*a* does not have a function of forming image data, for example, the above examination data (1) and/or (4) is input to the cloud server 100. In this case, the examination data processor 150 has the same function as that of the image forming unit 250. Besides, when the ophthalmic examination apparatus 200-*a* has a function of processing image data generated by the image forming unit 250, the examination data (4) may be obtained by the function. Examples of this function include fundus layer thickness analysis, drusen analysis, optic disc shape analysis, and the like (described later).

Although the examination data described above are obtained by OCT, the examination data may be data obtained by other tests. Examples of the other tests include subjective visual acuity test (described later). The examination data may include image data obtained by photographing the fundus or the anterior eye segment.

Described below are examples of processing performed by the examination data processor 150. As a first example, the examination data processor 150 may generate layer thickness information of the fundus based on examination data obtained by OCT. In other words, the examination data processor 150 can perform the fundus layer thickness analysis (retinal thickness analysis, RNFL thickness analysis, etc.). Further, the examination data processor 150 is capable of performing comparative analysis between the layer thickness information obtained by the fundus layer thickness analysis and standard layer thickness (e.g., standard value(s) of layer thickness corresponding to a healthy eye).

The fundus layer thickness analysis is a process of obtaining the (distribution of) thickness of a predetermined layer tissue of the fundus based on the examination data obtained by OCT. As an example, the retinal thickness analysis is explained below. Similar process is performed for determining the thickness of another layer tissue.

In the retinal thickness analysis, for example, a cross-sectional image or a three-dimensional image of the fundus is analyzed to obtain the thickness distribution of the retina in part or all of the scan area in OCT. Note that the retinal thickness has different definitions. For example, the retinal thickness may be defined as a thickness from the inner limiting membrane to the inner nuclear layer (inner segment and outer segment of photoreceptor cells), a thickness from the inner limiting membrane to the retinal pigment epithelium, or the like. The retinal thickness obtained by the retinal thickness analysis may be defined according to any of such known definitions.

For example, the retinal thickness analysis is performed in the following manner. First, an OCT image of the fundus is analyzed to specify an image area corresponding to a predetermined boundary site(s) (e.g., the inner limiting membrane and the retinal pigment epithelium). Then, the number of pixels between the specified boundary site(s) is counted to obtain the retinal thickness (i.e., distance in the depth direction). For the process of analyzing an OCT image to obtain the thickness of the fundus layer, reference may be had to, for example, Japanese Unexamined Patent Application Publication Nos. 2007-325831, 2008-206684, 2009-61203, and 2009-66015 filed by the present applicant.

The comparative analysis of the retinal thickness is an analysis of comparing the retinal thickness obtained by the retinal thickness analysis and standard data (i.e., normative data) stored in advance. The normative data indicates a standard value(s) of the retinal thickness (standard thickness) of the healthy eye. The normative data may be created by measuring the retinal thickness of a number of healthy eyes, and obtaining a statistical value(s) of the measurement results (average value, standard deviation, etc.). The comparative analysis determines whether the retinal thickness of the subject's eye E is within the range of that of healthy eyes. Incidentally, when the range of the retinal thickness of eyes with a disease is obtained in advance, the comparative analysis may be performed by determining whether the retinal thickness obtained by the retinal thickness analysis is within the range.

The examination data processor 150 may be configured to be capable of performing drusen analysis. The drusen analysis is a process of, for example, analyzing an OCT image to obtain the distribution of drusen in part or all of the scan area. The distribution may include the position, size (area, volume, diameter), or the like of the drusen in the fundus In the drusen analysis, for example, an OCT image is analyzed to specify an image area corresponding to the Bruch's membrane and an image area corresponding to the retinal pigment epithelium. Then, an image area corresponding to a small substantially circular raised shape is specified as (candidate of) drusen based on pixel values between these image areas. The process of specifying the image area based on such a shape can be carried out by, for example, image matching with a template of the shape. Further, the examination data processor 150 obtains the position, number, size, and the like of the drusen based on the image area corresponding to the drusen thus specified. Further, evaluation information can be generated for the state of age-related macular degeneration based on the distribution of the drusen acquired.

Incidentally, when the examination data includes the front image of the fundus, the drusen analysis can be performed based on the front image. In this drusen analysis, for example, it is determined whether the pixel value of each pixel in the front image falls within a predetermined range to specify pixels in the range. If the front image is a color image, drusen is illustrated in a specific color (yellowish white). Accordingly, a range of pixel values corresponding to the specific color is set, in advance, as the predetermined range mentioned above. Besides, if the front image is a monochrome image, drusen is illustrated with characteristic brightness (luminance). Accordingly, a range of pixel values corresponding to the characteristic brightness is set, in advance, as the predetermined range mentioned above. Further, an image area corresponding to drusen can be specified by performing template matching based on the standard form of drusen (small substantially circular raised shape) or the like.

The optic disc shape analysis may include an analysis process in which a cross-sectional image or a three-dimensional image of the fundus is analyzed to detect a hole (cut, defect site) in the retina, thereby determining the shape of the optic disc. In the optic disc shape analysis, for example, a cross-sectional image or the like is analyzed to specify an image area corresponding to the optic disc and the retinal surface around it. The image area thus specified is analyzed to obtain parameters (optic disc shape parameters) representing the global shape and the local shape (concavity and convexity) of the optic disc. Examples of the optic disc shape parameters include the cup diameter, disc diameter, and rim diameter of the optic disc, the depth of the optic disc, and the like.

In addition, the optic disc shape analysis may include an analysis process of obtaining a tilt of the optic disc (asymmetry of the shape). For example, this analysis process is performed in the following manner. First, the examination data processor 150 analyzes a three-dimensional image obtained by scanning an area including the optic disc to specify the center of the optic disc. Next, the examination data processor 150 sets a circular area centering around the specified center of the optic disc, and divides the circular area radially to obtain a plurality of partial areas. Subsequently, the examination data processor 150 analyzes a cross-sectional image of the circular area to obtain the height position of a predetermined layer (e.g., the retinal pigment epithelium layer) at each pixel location. Further, the examination data processor 150 calculates the average value of height positions of the predetermined layer for each of the partial areas. Next, the examination data processor 150 compares a pair of average values obtained for a pair of partial areas corresponding to opposite positions with respect to the center of the optic disc to obtain a tilt of the fundus in the corresponding direction. Then, the examination data processor 150 generates tilt distribution information indicating the distribution of the tilt of the fundus in the circular area based on the tilts obtained for a plurality of corresponding directions. Besides, evaluation information can be generated for the state of disease based on the tilt distribution information thus generated (and information indicating the standard distribution).

(Report Processor 160)

The cloud server 100 is configured to send examination data and analysis results received from each of the ophthalmic examination apparatuses 200-*a* to the attending physician of a corresponding patient user (e.g., to the diagnostician terminal 500-*d* or the medical staff terminal 650-*f*). Incidentally, the examination data (including image data)

may be sent to the doctor (radiologist) in charge of interpretation of images. The attending physician (or the radiologist) creates a diagnostic report (also referred to as a medical report, radiology report, etc.) based on the examination data, the analysis results, medical record information, and the like. The diagnostic report contains diagnosis results on the basis of the examination data, the analysis results, and the like. Examples of the diagnosis results include current disease state, time course of the disease state, necessity of dosing, changes in dosage, necessity of a hospital visit, and the like. The diagnostic report thus created is sent to the cloud server 100 from the diagnostician terminal 500-*d* and the like.

The report processor 160 performs a process related to a diagnostic report sent from each of the diagnostician terminals 500-*d* or the like. For example, the report processor 160 determines whether the diagnostic report contains a visit request for a patient. The visit request includes at least information indicating the necessity of a hospital visit (character string information, presence or absence of a check mark, etc.). The visit request may further include visit date and the like. For example, the report processor 160 obtains the necessity of a visit, the visit date, and the like based on information put in a predetermined visit request entry column. The process related to the visit request is described later with reference to FIGS. 6A and 6B.

The report processor 160 may perform a process of extracting predetermined information from the diagnostic report. The information extracted from the diagnostic report is, for example, stored in the patient information storage area 121 of the corresponding patient user. The information extracted from the diagnostic report is also sent to the patient terminal 300-*b* and/or the appointee terminal 400-*c* corresponding to the patient user.

(Accounting Processor 170)

The accounting processor 170 performs a process related to the use fee of the service that the cloud server 100 provides. The process performed by the accounting processor 170 includes a process of charging the user for the service and a process of calculating a fee for a predetermined user.

For example, the fee is charged to any one or more of the types of users including patient users, users related to the patients, medical institution users, financial institution users, and insurance provider users. Each service that involves a charge may be an option, or it may be a default. The fee occurs for any of medical institution users, examination apparatus installation institutions, and the system administering authority, for example. Incidentally, when an institution other than the system administering authority operates the examination data processing apparatus 900, the fee may occur for this institution.

Accounting process is described below. Examples of paid services that the cloud server 100 provides to patient users include the following:

Management of accounts by means of the patient information management unit 141;

Installation of the ophthalmic examination apparatus 200-*a* in a home or the like (rental, loan, buying and selling, etc.);

Examination using the ophthalmic examination apparatus 200-*a*; Processing of examination data by means of the examination data processor 150;

Provision of processing results of the examination data to the patient user, the users related to the patient, and the like;

Storage of the examination data in the account of the patient user;

Provision of maintenance service for the ophthalmic examination apparatus 200-*a*;

Provision of social networking services such as a blog function, a bulletin board function, and the like;

Provision of services that a financial institution user provides to the patient user on behalf of the financial institution; and Provision of services that an insurance provider user provides to the patient user on behalf of the insurance provider.

Examples of paid services that the cloud server 100 provides to users related to a patient user include the following:

Creation and management of account for the users related to the patient;

Provision of processing results of examination data to the users related to the patient;

Provision of social networking services such as a blog function, a bulletin board function, and the like;

Provision of services that a financial institution user provides to the users related to the patient on behalf of the financial institution; and Provision of services that an insurance provider user provides to the users related to the patient on behalf of the insurance provider.

Examples of paid services that the cloud server 100 provides to a medical institution user include the following:

Management of account by the medical institution information management unit 142;

Introduction of a new patient user to the medical institution user; Introduction of a patient user who wishes to be transferred to another hospital to the medical institution user;

Contingency fee for the introduction of a patient user;

Provision of statistical information obtained for a patient user;

Access to specific or non-specific patient users (questionnaires, etc.);

Access to other medical institution users (second opinion, referral letter, etc.);

Use of information related to analysis process (normative data, etc.);

Own or use of an ophthalmic examination apparatus (rental, loan, buying and selling, etc.);

Processing of examination data by the examination data processor 150;

Provision of processing results of the examination data to the medical institution user;

Management of examination data for a predetermined patient user by means of the account of the medical institution user;

Provision of maintenance service for the ophthalmic examination apparatus;

Provision of social networking services such as a blog function, a bulletin board function, and the like;

Provision of services that a financial institution user provides to the medical institution user on behalf of the financial institution;

Provision of services that an insurance provider user provides to the medical institution user on behalf of the insurance provider;

Provision of advertisement of the medical institution user to patient users and the like; and Contingency fee for the advertisement.

Examples of paid services that the cloud server 100 provides to a financial institution user include the following:

Creation and management of account for the financial institution user;

Provision of information on charges to users (debit amount, etc.);

Provision of social networking services such as a blog function, a bulletin board function, and the like;

Provision by the cloud server 100 of services that the financial institution user provides on behalf of the financial institution user;

Provision of advertisement of the financial institution user to patient users and the like; and Contingency fee for the advertisement.

Examples of paid services that the cloud server 100 provides to an insurance provider user include the following:

Creation and management of account for the insurance provider user;

Provision of information on the insurance of patient users (history of hospital visit, payments, etc.);

Provision of information on the insurance of medical institution users (medical remuneration points, receipts, etc.);

Provision of social networking services such as a blog function, a bulletin board function, and the like;

Provision by the cloud server 100 of services that the insurance provider user provides on behalf of the insurance provider user;

Provision of advertisement of the insurance provider user to patient users and the like; and Contingency fee for the advertisement.

The accounting processor 170 stores in advance a fee for each paid service. This information is, for example, table information associating the types of the paid services with fees to be charged. When a paid service is provided to a certain user, the arithmetic and control unit 110 sends the user ID of the user and information indicating the type of the service to the accounting processor 170. The accounting processor 170 acquires the amount of a fee to be charged corresponding to this type information with reference to the table information. Then, the accounting processor 170 associates the amount of the fee with the user ID, and sends them to the arithmetic and control unit 110. The arithmetic and control unit 110 sends the information received from the accounting processor 170 to the user information management unit 140. The user information management unit 140 stores the amount of the fee in an account identified by the user ID. At this time, information related to the service (provision date and time, type, etc.) can be stored with the amount of the fee.

A description is given of the process of fee calculation. As described above, a payment occurs for any of, for example, medical institution users, examination apparatus installation institutions, and the system administering authority.

For example, when charging (system use fee) as described above has occurred, the accounting processor 170 calculates the amount of the fee based on the system use fee. When, for example, a medical institution user has made a report after an examination performed using the ophthalmic examination apparatus 200-*a*, and at least part of the report has been sent to a patient user or those related to the patient, the accounting processor 170 calculates the amount of a fee for each of the medical institution user, an institution where the ophthalmic examination apparatus 200-*a* is installed, and the system administering authority based on the amount of a fee to be charged and the fee calculation rule 126. Incidentally, when an institution other than the system administering authority operates the examination data processing apparatus 900, and an analysis process is performed by the examination data processing apparatus 900, a fee is calculated for the administering authority of the examination data processing apparatus 900. Such a calculation process of a fee is explained in the description of the fee calculation rule 126.

(Insurance Processor 180)

The insurance processor 180 performs a process related to insurance. Incidentally, the accounting processor 170 may be configured to perform the accounting process and the fee calculation process for paid services related to insurance. The insurance processor 180 performs, for example, a process related to insurance contract already concluded between a certain patient user and a certain insurance provider user. As described above, the storage 120 (e.g., the patient information storage area 121 and the insurance provider information storage area 125) stores information indicating the relationship between the insurance provider user and the patient user. This information is, for example, table information associating the user ID of the patient user with the user ID of the insurance provider user. With reference to such information, the insurance processor 180 can determine an insurance provider(s) that a certain patient user has a contract with, and, on the contrary, a patient user(s) that a certain insurance provider has a contract with.

As a specific example, when a patient user receives medical practice in a medical institution, the cloud server 100 retrieves preset information (disease name, medical fee, etc.) from the medical institution server 600-*e* of the medical institution together with the patient user ID. For example, with reference to the table information described above, the insurance processor 180 specifies an insurance provider user that corresponds to the patient user. The arithmetic and control unit 110 controls the communication unit 130 to send (at least part of) the information retrieved from the medical institution server 600-*e* to the insurance provider user specified by the insurance processor 180.

When a medical institution user has made a report after an examination performed using the ophthalmic examination apparatus 200-*a*, and at least part of the report has been sent to a patient user or those related to the patient, the insurance processor 180 may perform the following process. First, the insurance processor 180 specifies the user ID of the insurance provider user associated with the user ID of the patient user with reference to the table information described above. In other words, the insurance processor 180 specifies the insurance provider user that the patient user has made a contract with. Further, the insurance processor 180 sends the patient user ID, the user ID of the insurance provider user thus specified, and information indicating the amount of a fee to be charged to the arithmetic and control unit 110. The arithmetic and control unit 110 controls the communication unit 130 to send the patient user ID and the information indicating the amount of the fee to the insurance provider server 800-*h* of the insurance provider user.

[Ophthalmic Examination Apparatus 200-*a*]

Described below is an example of the configuration of the ophthalmic examination apparatus 200-*a*. The ophthalmic examination apparatus 200-*a* is used for optical examination of the subject's eye. The ophthalmic examination apparatus 200-*a* has a function as an ophthalmologic imaging apparatus and/or a function as an ophthalmic measurement apparatus. Examples of the ophthalmic imaging apparatus include optical coherence tomography (OCT device), fundus camera, scanning laser ophthalmoscope, and the like. Examples of the ophthalmic measurement apparatus include eye refraction test device, tonometer, specular microscope, wave front analyzer, and the like. In this embodiment, the application of the OCT device is described in detail; however, this embodiment can be applied to any other ophthalmic examination apparatuses.

Incidentally, an image acquired by OCT may be referred to as OCT image in this specification. In addition, a measurement operation for forming an OCT image may be referred to as OCT measurement in this specification.

In this embodiment, a description is given of a so-called spectral-domain OCT device including a low-coherence light source and a spectrometer; however, this embodiment can be applied to other types of OCT devices such as, for example, swept-source OCT devices. The swept-source OCT is a technique for imaging the morphology (structure) of an object to be measured in the following manner. First, the wavelength of light irradiated to the object is varied (wavelength sweep). Next, reflected light of each wavelength and reference light are superposed to generate interference light, and the interference light is sequentially detected to obtain spectral intensity distribution. Then, Fourier transform is applied to the spectral intensity distribution.

The ophthalmic examination apparatuses 200-*a* according to the embodiment may have an imaging function other than OCT. As an example of the additional imaging function may be cited a function of capturing a front image of the anterior segment and/or the fundus of the eye. This may be realized by, for example, the similar configuration to a conventional fundus camera.

Described below is the configuration of the ophthalmic examination apparatus according to the embodiment. The system of this embodiment includes a plurality of ophthalmic examination apparatuses 200-*a*. FIG. 3 illustrates an example of the configuration of the ophthalmic examination apparatus 200-*a*. As illustrated in FIG. 3, the ophthalmic examination apparatus 200-*a* includes an optical unit 210, a computer 230, and a user interface (UI) 280.

(Optical Unit 210)

The optical unit 210 includes an optical system for performing OCT measurement and a mechanism for driving a predetermined optical element. The optical system splits light from a light source 211 into measurement light and reference light, superposes the measurement light returning from the subject's eye E and the reference light, and detects interference light thus generated. The optical system has the same configuration as a conventional spectral-domain OCT device. That is, the optical system is configured to divide low-coherence light (broad band light) into reference light and measurement light, superposes the measurement light having passed through the subject's eye E and the reference light having propagated through the reference optical path to generate interference light, and detects spectral components of the interference light. The detection result of the spectral components (detection signals) is sent to the computer 230.

If swept-source OCT is used, the low-coherence light source is replaced by a wavelength-swept light source (wavelength tunable light source), and an optical member is not provided for spectral decomposition of interference light. Besides, for example, a balanced photodiode is provided as an element for detecting the interference light. In general, a known technology can be arbitrarily applied to the configuration of the optical unit 210 according to the type of OCT.

The light source 211 outputs broad band, low-coherence light. The low-coherence light includes, for example, wavelength bands in the near-infrared region (about 800 nm to 900 nm), and has a temporal coherence length of about several tens of micrometers. Incidentally, the low-coherence light may be near infrared light of wavelengths invisible to the human eye, for example, with a center wavelength of about 1040 nm to 1060 nm.

The light source 211 includes a light output device, such as a super luminescent diode (SLD), a light-emitting diode (LED), a semiconductor optical amplifier (SOA), or the like.

The low-coherence light output from the light source 211 is collimated into a parallel light beam by a collimator lens 212 and guided to a beam splitter 213. The beam splitter 213 is, for example, a half mirror that reflects a predetermined proportion of light and transmits the rest. The beam splitter 213 splits the parallel light beam into measurement light and reference light.

The measurement light is light that is irradiated to the subject's eye E (also referred to as signal light). A group of optical elements which forms the optical path of the measurement light (measurement optical path) is referred to as a measurement arm (also referred to as sample arm, etc.). The reference light serves as a reference to extract information contained in return light of the measurement light as an interference signal. A group of optical elements which forms the optical path of the reference light (reference optical path) is referred to as a reference arm.

The beam splitter 213 is arranged at one end of the reference optical path, and a reference mirror 214 is arranged at the other end. The reference light formed of components having transmitted through the beam splitter 213 is reflected by the reference mirror 214, and returned to the beam splitter 213.

By a reference mirror driver 214A illustrated in FIG. 4, the reference mirror 214 is moved along the traveling direction of the reference light. Thereby, the length of the reference optical path is changed. The reference mirror driver 214A functions to relatively change the length of the measurement optical path and the length of the reference optical path to thereby change the depth position where the intensity of interference between the measurement light and the reference light becomes maximum. Such an operation of changing the interference depth is an example of the operation of changing the focus position of the measurement light.

In this embodiment, a configuration is employed in which the length of the reference optical path is changed. Instead of or in addition to this configuration, there may be provided a configuration to change the length of the measurement optical path. The length of the measurement optical path can be changed by, for example, introducing a corner cube that reflects incident measurement light in a direction opposite to the incident direction and a mechanism for moving the corner cube in the incident direction and the reflection direction.

The measurement light formed of components reflected by the beam splitter 213 is deflected by a fixed mirror 215 arranged to be inclined with respect to the measurement optical path, and is guided to a scanner 216. The scanner 216 is, for example, a two-axis optical scanner. This means that the scanner 216 may be configured to be capable of two-dimensionally deflecting the measurement light. The scanner 216 is, for example, a mirror scanner including two mirrors which can turn in directions perpendicular to each other. The mirror scanner is configured as, for example, a micro-electro-mechanical systems (MEMS). As another example, the scanner 216 may be formed by using a mirror scanner and a rotary prism.

The measurement light output from the scanner 216 is collimated light that has been two-dimensionally deflected. This measurement light is converted into converging light by a relay lens 217, and intermediately forms an image in a plane (fundus conjugate plane) Pc conjugate to the fundus Ef. Further, the measurement light is once again converged by an objective lens 219 having the function of a focusing lens, and is incident on the subject's eye E. Incidentally, an optical element (dichroic mirror 218) arranged in the fundus conjugate plane Pc is described later.

The objective lens 219 and a lens barrel 219A are moved along the measurement optical path by a lens barrel driver 219B illustrated in FIG. 4. The objective lens 219 and the lens barrel 219A are moved in the optical axis direction according to the refractive power of the subject's eye E. Thus, the fundus conjugate plane Pc can be located in a position conjugate to the fundus Ef. As a result, the measurement light is projected onto the fundus Ef as a spot light. The objective lens 219 (and the lens barrel driver 219B) functions as a diopter correction unit that corrects the eye diopter, and also a focus position changing unit that changes the focus position of the measurement light.

Described blow is another example of the diopter correction unit. For example, to deal with the subject's eye with an extreme refractive power like high myopia, a diopter correction lens can be arranged in the measurement optical path. For example, there may be a mechanism (not illustrated) to place/remove the diopter correction lens on/from the measurement optical path. Besides, it is also possible to use an optical element having a variable refractive power like, for example, Alvarez lens. Such an optical element for diopter correction is located, for example, between the subject's eye E and the objective lens 219.

The measurement light irradiated to the fundus Ef is scattered (reflected) at various depth positions of the fundus Ef. The backscattered light (return light) of the measurement light from the fundus Ef travels the same path in the reverse direction and is guided to the beam splitter 213.

The beam splitter 213 causes the return light of the measurement light to interfere with the reference light having passed through the reference optical path. At this time, components of the return light which have traveled about the same distance as the length of the reference optical path, i.e., only the backscattered light from the range within the coherence length with respect to the length of the reference optical path, substantially interfere with the reference light. The interference light generated through the beam splitter 213 is guided to a spectroscope 220. The interference light incident on the spectroscope 220 is dispersed (spectrally resolved) by a diffraction grating 221, and projected on a light receiving surface of the CCD image sensor 223 through a lens 222. Although FIG. 4 illustrates a transmissive diffraction grating as the diffraction grating 221, the diffraction grating 221 may be formed with a spectral element of other forms, such as, for example, a reflection diffraction grating.

The CCD image sensor 223 is, for example, a line sensor. The CCD image sensor 223 detects each spectral component of the dispersed interference light, and converts it to electric charges. The CCD image sensor 223 accumulates the electric charges to generate a detection signal, and sends it to the computer 230.

As described above, the dichroic mirror 218 is arranged to be inclined in a position corresponding to the fundus conjugate plane Pc of the measurement optical path. The dichroic mirror 218 is configured to transmit measurement light in the near-infrared band therethrough and reflect light in the visible bands.

A flat panel display (FPD) 225 and a lens 226 are arranged in an optical path branched from the measurement optical path via the dichroic mirror 218. The flat panel display 225 displays information under the control of a controller 240. As an example of the information displayed on the flat panel display 225 may be cited various types of visual targets to be presented to the subject's eye E. Examples of the visual targets include optotypes (Landolt rings) for subjective visual acuity test, a fixation target to help the subject's eye E to fixate, and the like.

The flat panel display 225 is located in a position conjugate to the fundus conjugate plane Pc (i.e., a position conjugate to the fundus Ef) through the lens 226. The flat panel display 225 may be, for example, a liquid crystal display (LCD) or an organic electroluminescence display (OELD).

Visible light output from the flat panel display 225 is reflected to the dichroic mirror 218 through the lens 226. The visible light is incident on the subject's eye E through the objective lens 219, and reaches the fundus Ef. Thereby, an image (e.g., visual target image) based on the visible light is projected onto the fundus Ef.

An optical element such as a half mirror may be provided in place of the dichroic mirror 218. It is also possible to provide a reflection mirror that can be placed on and removed from the measurement optical path. If the dichroic mirror 218, a half mirror, or the like is provided, the projection of a visual target can be performed simultaneously with OCT measurement. On the other hand, when a reflection mirror is provided, OCT measurement and the projection of a visual target are performed at different timings.

While this embodiment employs a Michelson interferometer, it is possible to use any type of interferometer, such as, for example, a Mach-Zehnder interferometer. Further, in place of the CCD image sensor, it is possible to use a light receiving element of another form, such as, for example, a complementary metal-oxide semiconductor (CMOS) image sensor.

In this embodiment, the light reflected by the beam splitter 213 is used as the measurement light, and the light having transmitted through it is used as the reference light. On the contrary, the light reflected by the beam splitter 213 may be used as the reference light, and the light having transmitted through it may be used as the measurement light. In this case, the arrangement of the measurement arm and the reference arm is reversed from that of FIG. 3.

There may be provided a member for converting the properties of the measurement light and/or the reference light. For example, an optical attenuator and a polarization adjuster (polarization controller) may be provided in the reference optical path. The optical attenuator may be configured to adjust the amount of the reference light under the control of the computer 230. The optical attenuator includes, for example, a neutral density filter and a mechanism for inserting/removing it into/from the reference optical path. The polarization adjuster may be configured to adjust the polarization state of the reference light under the control of the computer 230. The polarization adjuster includes, for example, a polarizing plate arranged on the reference optical path, and a mechanism for rotating it. These are used to adjust the intensity of interference between the return light of the measurement light and the reference light.

A front image acquisition optical system may be provided to capture a front image of the subject's eye E. The front image is an image of the anterior segment or the fundus Ef of the eye. The front image acquisition optical system forms an optical path branched from the measurement optical path, and includes, for example, an illumination optical system and an imaging optical system similar to those of the conventional fundus camera. The illumination optical system irradiates illumination light consisting of (near) infrared light or visible light to the subject's eye E. The imaging optical system detects the illumination light returning from the subject's eye E (reflected light). The imaging optical system includes a zoom lens system. The imaging optical system shares a common focusing lens (the objective lens 219, the diopter correction lens, etc.) with the measurement optical path, and/or includes a focusing lens separately from the measurement optical path. As another example of the front image acquisition optical system may be cited the same optical system as the conventional SLO.

If there is the front image acquisition optical system, it is possible to further provide an alignment optical system as in the conventional fundus camera. The alignment optical system is configured to form an optical path branched from the measurement optical path, and generates an index (alignment index) to align the optical system of the apparatus with the subject's eye E. The alignment includes: xy alignment in a direction (referred to as xy direction) along a plane perpendicular to the measurement optical path (the optical axis of the objective lens 219); and z alignment in the z direction perpendicular to the xy direction. Although not illustrated, the alignment optical system generates two alignment light beams by a two-hole aperture from a light beam output from an alignment light source (LED, etc.). The two alignment light beams are guided to the measurement optical path via a beam splitter arranged to be inclined with respect to the measurement optical path. Thus, the alignment light beams are projected onto the subject's eye E. The alignment light beams reflected from the cornea are detected by the image sensor of the front image acquisition optical system.

If there is the alignment optical system, automatic alignment can be performed. Specifically, a data processor 260 of the computer 230 analyzes a signal received from the image sensor of the front image acquisition optical system, and specifies the positions of the images of the two alignment indices (alignment index images). Further, based on the positions of the two alignment index images specified, the controller 240 moves the optical unit 210 such that two cornea reflection light beams are projected as being overlapped each other onto a predetermined position (e.g., the center position) on the light receiving surface of the image sensor. Incidentally, a unit driver 210A is provided to move the optical unit 210.

As another example of the alignment system may be cited a configuration using a pair of anterior segment cameras disclosed in Patent Document 7. The ophthalmic examination apparatus of this example includes a support for supporting the face of the subject, and a driver configured to move an optical system for testing the subject's eye E and the support relatively and three-dimensionally. A pair of anterior segment cameras substantially simultaneously photographs the anterior segment of the subject's eye E from different directions from each other. The data processor 260 of the computer 230 analyzes the two anterior segment images captured at substantially the same time by the pair of anterior segment camera to thereby obtain the three-dimensional position of the subject's eye E. The controller 240 controls the driver based on the three-dimensional position to relatively move the optical system and the support. This control is performed such that the optical axis of the optical system passes through the three-dimensional position of the subject's eye E, and also the distance between the three-dimensional position and the optical system (the objective lens 219) is adjusted to a predetermined working distance. According to this alignment method, there is an advantage in that all processes from the search of the subject's eye E to the three-dimensional alignment of the optical system can be performed automatically. Note that, in the case of using an alignment index, it is required to manually guide the optical system such that the alignment index is projected onto the subject's eye E.

If there is the front image acquisition optical system, it is possible to further provide a focusing optical system as in the conventional fundus camera. The focusing optical system is configured to form an optical path branched from the measurement optical path, and generates an index (split index) for focusing on the fundus Ef. Although not illustrated, the focusing optical system generates two focusing light beams by a split target plate from a light beam output from a focusing light source (LED, etc.). The two focusing light beams are guided to the measurement optical path via a reflective member arranged to be inclined with respect to the measurement optical path. Thus, the focusing light beams are projected onto the fundus Ef. The focusing light beams reflected from the fundus are detected by the image sensor of the front image acquisition optical system.

If there is the focusing optical system, automatic focusing can be performed. Specifically, the data processor 260 of the computer 230 analyzes a signal received from the image sensor of the front image acquisition optical system, and specifies the positions of the images of the two split indices (split index images). Further, based on the positions of the two split index images specified, the controller 240 performs the movement control of the focusing optical system as well as control of the focusing lens (the movement control of the objective lens 219, the insertion/removal control of the diopter correction lens, or the like) such that two light beams reflected from the fundus are projected on a straight line on the light receiving surface of the image sensor.

If there is the front image acquisition optical system, it is possible to perform automatic tracking. In automatic tracking, the optical unit 210 moves in accordance with the movement of the subject's eye E. To perform automatic tracking, alignment and focusing are performed in advance. The automatic tracking is performed, for example, in the following manner. First, the front image acquisition optical system captures a moving image of the subject's eye E. The data processor 260 sequentially analyzes frames of the moving image to monitor the movement (positional change) of the subject's eye E. The controller 240 controls the unit driver 210A to move the optical unit 210 according to the positions of the subject's eye E successively obtained. Thereby, the optical unit 210 can follow the movement of the subject's eye E in real time. Thus, it is possible to maintain a suitable positional relationship with proper alignment and focus.

(Control System and Data Processing System)

Described below are the control system and the data processing system of the ophthalmic examination apparatus 200-*a* according to the embodiment. FIG. 4 illustrates an example of the configuration of the control system and the data processing system.

The computer 230 is the center of the control system and the data processing system. The computer 230 includes a microprocessor, RAM, ROM, a hard disk drive, a communication interface, and the like. Computer programs for implementing various types of processing on the ophthalmic examination apparatus 200-*a* are stored in a storage device such as a hard disk drive. The computer 230 may have a dedicated circuit board to perform specific processing. For example, the computer 230 may be provided with a circuit board for implementing processing of forming an OCT image.

(User Interface 280)

The user interface 280 is connected to the computer 230. The user interface 280 includes a display 281 and an operation unit 282. The display 281 includes a display device such as a flat panel display or the like. The operation unit 282 includes operation devices such as a button, a key, a joystick, an operation panel, which are arranged on the housing of the ophthalmic examination apparatus 200-a and/or outside the ophthalmic examination apparatus 200-a. If the computer 230 includes a personal computer, the operation unit 282 may include an operation device of the personal computer (a mouse, a keyboard, a track pad, a button, etc.).

The display 281 and the operation unit 282 need not necessarily be configured as separate devices, and they may be a device having a display function integrated with an operation function, like, for example, a touch panel. In this case, the operation unit 282 may include the touch panel and a computer program. The content of operation performed on the operation unit 282 is input to the controller 240 as an electrical signal. Further, operation, data input, and the like may be performed by using a graphical user interface (GUI) displayed on the display 281 and the operation unit 282.

(Controller 240)

The controller 240 is provided in the computer 230. The controller 240 includes a microprocessor, RAM, ROM, a hard disk drive, and the like. The controller 240 includes a main controller 241 and a storage 242.

(Main Controller 241)

The main controller 241 controls each unit in the ophthalmic examination apparatus 200-a. For example, the main controller 241 controls the unit driver 210A, the light source 211, the reference mirror driver 214A, the scanner 216, the lens barrel driver 219B, the CCD (image sensor) 223, the flat panel display 225, the display 281, the data processor 260, and a communication unit 270.

The unit driver 210A includes a mechanism for moving the optical unit 210 in a direction (z direction) along the measurement optical path (the optical axis of the objective lens 219) and a direction (xy direction) along a plane perpendicular to the z direction. The reference mirror driver 214A moves the reference mirror 214 along the reference optical path. The lens barrel driver 219B moves the objective lens 219 and the lens barrel 219A along the measurement optical path.

(Storage 242)

The storage 242 stores a variety of data. The storage 242 also stores various types of computer programs and data for operating the ophthalmic examination apparatus 200-a. The data stored in the storage 242 includes data obtained by the ophthalmic examination apparatus 200-a, and data stored in advance. The computer programs are designed to operate the ophthalmic examination apparatus 200-a in conjunction with, for example, the cloud server 100.

Examples of the data obtained by the ophthalmic examination apparatus 200-a include image data of an OCT image, examination data, image data of a front image, and the like. The examination data may include data indicating the state of the subject's eye (described in detail later), which is generated by processing the detection result of the interference light obtained by the optical unit 210. The examination data may include visual acuity value data obtained by subjective visual acuity test and data generated by processing the image data of a front image.

Examples of data stored in the storage 242 include setting information as described below. The setting information is information in which contents of settings related to the optical unit 210 and the data processor 260 are recorded. The setting information is, for example, acquired from the cloud server 100 and stored in the storage 242. As a specific example, in response to the input of a patient user ID (and authentication information), the controller 240 sends it with an apparatus ID to the cloud server 100 by controlling the communication unit 270. Setting information is stored in advance for each patient user in the patient information storage area 121. The patient information management unit 141 retrieves the setting information corresponding to the patient user ID. The arithmetic and control unit 110 controls the communication unit 130 based on the apparatus ID to thereby send the setting information retrieved to the ophthalmic examination apparatus 200-a. The main controller 241 of the ophthalmic examination apparatus 200-a stores, in the storage 242, the setting information received by the communication unit 270. The main controller 241 controls each unit of the ophthalmic examination apparatus 200-a on the basis of the setting information, thereby performing the examination of the subject's eye E.

Described below are examples of the setting information. The setting information may contain the content of setting related to, for example, at least one of the following items: (1) fixation position; (2) scan pattern; (3) focus position; (4) diopter correction value; and (5) analysis process. The fixation position refers to the direction in which the subject's eye E is made to fixate.

(1) The "fixation position" indicates the direction in which the subject's eye E is made to fixate, in other words, a site of the subject's eye E to which OCT measurement is applied. Examples of the fixation position include a fixation position for OCT measurement of the macula and its periphery, a fixation position for OCT measurement of the optic disc and its periphery, a fixation position for OCT measurement of the macula, the optic disc, and their peripheries, and the like. A fixation position may be set correspondingly to an arbitrary site of the subject's eye E. The fixation position includes, for example, information indicating the display position (the positions of pixels) of the fixation target on the flat panel display 225.

(2) The "scan pattern" indicates a pattern along which the projection position of the measurement light is moved with respect to the subject's eye E. Examples of the scan pattern include one or more line scans (horizontal scan, vertical scan), one or more cross-scans, a radial scan, a circle scan, and the like. To acquire a three-dimensional image (three-dimensional data set), a three-dimensional scan pattern is employed in which a plurality of scan lines are arranged at sufficiently narrow intervals.

(3) The "focus position" indicates focus conditions applied in OCT measurement. The focus position includes, for example, information indicating the position of the objective lens 219.

(4) The "diopter correction value" indicates conditions used in diopter correction. Specific examples of the diopter correction value include a value indicating the refractive power (visual acuity) of the subject's eye E, use/non-use of a diopter correction lens, a value indicating the refractive power to be applied by the diopter correction lens.

(5) The "analysis process" indicates the content of processing performed based on data acquired by the optical unit 210, i.e., the type of examination data to be acquired. As with the cloud server 100, examples of the analysis process include fundus layer thickness analysis, drusen analysis, optic disc shape analysis, and the like. The fundus layer thickness analysis is a process of obtaining the thickness of a predetermined layer tissue (retina, sub-tissue of the retina, choroid, sclera, etc.) of the fundus. The drusen analysis is a process of obtaining the distribution of drusen (mass of waste products) to be used as a diagnostic material for age-related macular degeneration. The optic disc shape analysis is a process of analyzing a cross-sectional image or a three-dimensional image of the fundus to detect a hole (cut, defect site) in the retina, thereby determining the shape of the optic disc. In the optic disc shape analysis, a tilt of the optic disc (asymmetry of the shape) can also be obtained. These analysis processes are described in detail later.

When OCT measurement is performed for both the left and right eyes of the subject, especially when different settings are used for the left and right eyes, setting information for the left eye (left eye setting information) and setting information for the right eye (right eye setting information) may be provided separately.

The setting information is created with reference to examination results and examination conditions of the subject's eye E, the disease name (the type of data to be used for diagnosis, etc.), and the like. For example, the fixation position is set with reference to the fixation positions used in the past OCT measurements, the disease name, and the like. The scan pattern is set with reference to the scan patterns used in the past OCT measurements, the disease name, and the like. The focus position is set with reference to the focus positions used in the past OCT measurements. The diopter correction value is set with reference to the visual acuity and the refractive power obtained in the past examinations, and the like. The analysis process is set with reference to the type of analysis processes used in the past examinations, the disease name, and the like.

Described below are specific examples of the relationship between examination results, examination conditions and/or the disease name, and the content of the setting. In a macula test, any of settings as follows can be employed:

(1) Used as the fixation position is a fixation position where the macula is included in the scan area, for example, a fixation position where the macula is located on the extension line of the optical axis of the measurement optical path.

(2) As the scan pattern, a three-dimensional scan pattern, a radial scan pattern and/or a line scan pattern are/is used.

(3) Used as the focus position is a focus position applied in the past OCT measurement, or a focus position obtained by calculation from the measurement value (eye axial length, refractive power, etc.) of the subject's eye E.

(4) Used as the diopter correction value is a diopter correction value applied in the past OCT measurement, or a diopter correction value obtained from the measurement value of the refractive power of the subject's eye E.

(5) As the analysis process, the fundus layer thickness analysis (and comparative analysis with the standard layer thickness) is used. In the fundus layer thickness analysis, for example, the thickness of the retina is determined (retinal thickness analysis).

In an optic disc test, any of settings as follows can be employed:

(1) Used as the fixation position is a fixation position where the optic disc is included in the scan area, for example, a fixation position where the optic disc is located on the extension line of the optical axis of the measurement optical path.

(2) As s the scan pattern, a three-dimensional scan pattern and/or a circle scan pattern are/is used.

(3) Used as the focus position is a focus position applied in the past OCT measurement, or a focus position obtained by calculation from the measurement value (eye axial length, refractive power, etc.) of the subject's eye E.

(4) Used as the diopter correction value is a diopter correction value applied in the past OCT measurement, or a diopter correction value obtained from the measurement value of the refractive power of the subject's eye E.

(5) As the analysis, the fundus layer thickness analysis (and comparative analysis with the standard layer thickness) and/or the optic disc shape analysis are/is used. In the fundus layer thickness analysis, for example, the thickness of the retinal nerve fiber layer is obtained (RNFL thickness analysis).

In a glaucoma test, any of settings as follows can be employed:

(1) Used as the fixation position is a fixation position where the macula is included in the scan area (e.g., a fixation position where the macula is located on the extension line of the optical axis of the measurement optical path), and/or a fixation position where the optic disc is included in the scan area (e.g., a fixation position where the optic disc is located on the extension line of the optical axis of the measurement optical path).

(2) As the scan pattern, a three-dimensional scan pattern is used.

(3) Used as the focus position is a focus position applied in the past OCT measurement, or a focus position obtained by calculation from the measurement value (eye axial length, refractive power, etc.) of the subject's eye E.

(4) Used as the diopter correction value is a diopter correction value applied in the past OCT measurement, or a diopter correction value obtained from the measurement value of the refractive power of the subject's eye E.

(5) Used as the analysis process is at least one of the retinal thickness analysis (and comparative analysis with the standard layer thickness), the RNFL thickness analysis (and comparative analysis with the standard layer thickness), and the optic disc shape analysis.

In an age-related macular degeneration test, any of settings as follows can be employed:

(1) Used as the fixation position is a fixation position where the macula is included in the scan area, for example, a fixation position where the macula is located on the extension line of the optical axis of the measurement optical path.

(2) As the scan pattern, a three-dimensional scan pattern is used.

(3) Used as the focus position is a focus position applied in the past OCT measurement, or a focus position obtained by calculation from the measurement value (eye axial length, refractive power, etc.) of the subject's eye E.

(4) Used as the diopter correction value is a diopter correction value applied in the past OCT measurement, or a diopter correction value obtained from the measurement value of the refractive power of the subject's eye E.

(5) As the analysis process, the retinal thickness analysis (and comparative analysis with the standard layer thickness), and/or drusen analysis are/is used.

The setting information can also be edited. For example, the attending physician or the like can edit (rewrite, add, delete, etc.) information related to examination results, examination conditions of the subject's eye E, the disease name, and the like with reference to the electronic medical record of the subject. In addition, comparing the settings used in a test conducted at a medical institution with the current setting information, the setting information can be edited automatically or manually based on the result of the comparison.
(Image Forming Unit 250)

The image forming unit 250 generates image data of a two-dimensional cross-sectional image of the subject's eye E based on a detection signal from the CCD image sensor 223. This process includes, as with the conventional spectral-domain OCT, noise removal (noise reduction), filtering, dispersion compensation, fast Fourier transform (FFT), and the like. If another type of OCT is employed, the image forming unit 250 performs a known process according to the type.

The image forming unit 250 includes, for example, a dedicated circuit board and/or a microprocessor. Incidentally, "image data" may be herein identified as "image" based on it.

The cloud server 100 can be provided with part or all of the functions of forming an OCT image. If the cloud server 100 has all the functions for forming an OCT image, it is not necessary that the ophthalmic examination apparatus 200-*a* is provided with the image forming unit 250.

When the ophthalmic examination apparatus 200-*a* is not provided with the image forming unit 250, the main controller 241 controls the communication unit 270 to send a detection signal (detection data) from the CCD image sensor 223 or data obtained by processing the detection data to the cloud server 100. The examination data processor 150 of the cloud server 100 generates image data of a two-dimensional cross-sectional image of the subject's eye E based on the data received from the ophthalmic examination apparatus 200-*a*.

If both the ophthalmic examination apparatus 200-*a* and the cloud server 100 have the image forming function, for example, image data of a two-dimensional cross-sectional image of the subject's eye E can be generated by the cooperation between the image forming unit 250 and the examination data processor 150. As another example of processing in this case, when the cloud server 100 has a heavy processing load, the ophthalmic examination apparatus 200-*a* may perform the image forming process. On the other hand, when having a lower processing load, the cloud server 100 may perform the image forming process. For example, the arithmetic and control unit 110 make the determination on the processing load. The usage conditions of the plurality of the ophthalmic examination apparatuses 200-*a* can be taken into account in the determination on the processing load.
(Data Processor 260)

The data processor 260 performs various types of data processing. For example, the data processor 260 performs image processing on an image formed by the image forming unit 250. As an example thereof, the data processor 260 can generate image data of a three-dimensional image of the subject's eye E based on a plurality of two-dimensional cross-sectional images of different cross-sections. The image data of a three-dimensional image is image data in which the positions of pixels are defined by the three-dimensional coordinate system. As one example of the image data of a three-dimensional image may be cited image data formed of three-dimensional arrays of voxels. This image data is referred to as volume data or voxel data. When displaying an image based on volume data, the data processor 260 performs rendering on the volume data (volume rendering, maximum intensity projection (MIP), etc.) to generate image data of a pseudo three-dimensional image viewed from a certain sight line direction. The data processor 260 can generated an image a desired cross-section of a three-dimensional image (multi-planar reconstruction (MPR)).

Besides, stack data of a plurality of cross-sectional images may be generated as the image data of a three-dimensional image. The stack data is image data obtained by three-dimensionally arranging a plurality of cross-sectional images acquired along a plurality of scan lines based on the positional relationship between the scan lines. That is, the stack data is image data obtained by representing a plurality of cross-sectional images, which have been originally defined by their individual two-dimensional coordinate systems, by a single three-dimensional coordinate system (i.e., embedding them in one three-dimensional space). The data processor 260 is capable of performing MPR based on the stack data.

The data processor 260 includes, for example, a microprocessor, RAM, ROM, a hard disk drive, a circuit board dedicated for predetermined data processing, and the like. A storage device such as a hard disk drive stores in advance a computer program for the microprocessor to perform data processing described below.

The data processor 260 includes an examination data generating unit 261, a stationary determination unit 262, and a left/right determination unit 263.
(Examination Data Generating Unit 261)

The examination data generating unit 261 processes the detection result of the interference light obtained by the optical unit 210, and thereby generates examination data that indicates the state of the subject's eye E. The examination data generating unit 261 is an example of a processor. The examination data generating unit 261 processes, for example, any of the following as the "detection result of the interference light":

(1) Signal output from the CCD image sensor 223;
(2) Image data generated by the image forming unit 250;
(3) Data obtained in the middle of the process performed by the image forming unit 250 (i.e., data obtained in the middle of the image data forming process); and
(4) Data obtained by processing signals output from the CCD image sensor 223 by means of a component other than the image forming unit 250.

Processing performed by the examination data generating unit 261 may include, for example, fundus layer thickness analysis (retinal thickness analysis, RNFL thickness analysis, etc.), comparative analysis of retinal thickness, drusen analysis, optic disc shape analysis, and the like.

If the flat panel display 225 can display optotypes (Landolt rings, etc.) for the subjective visual acuity test, the examination data generating unit 261 may generate examination data that includes a result of the subjective visual acuity test. The subjective visual acuity test is carried out in such a manner that the subject responds to the optotypes presented to the subject's eye E. According to a predetermined computer program, the examination data generating unit 261 repeats the process of determining whether or not the response from the subject is correct and the process of selecting a visual target to be presented next depending on the determination result. The main controller 241 displays the visual target selected by the examination data generating unit 261 on the flat panel display 225. By repeating these processes, the examination data generating unit 261 finds the visual acuity value of the subject's eye E, and generates examination data including the visual acuity value.
(Stationary Determination Unit 262)

The stationary determination unit 262 determines whether the subject's eye E is substantially stationary based on data acquired by the optical unit 210 (stationary determination). The term "substantially stationary" indicates not only the state where the subject's eye E is stationary, but also the state where the subject's eye E has a level of movement that does not affect OCT measurement. An acceptable range of this movement is arbitrarily set in advance.

Described below are examples of the stationary determination process. As a first example, the stationary determination is made based on the intensity of the return light of the measurement light. The intensity of the return light of the measurement light becomes maximum when the alignment is correct (because the regular reflection from the cornea is maximum). The intensity of the return light can be obtained by, for example, detecting part of the return light with a photodetector or the like. The stationary determination unit 262 can determine whether the subject's eye E is substantially stationary based on a time course of the intensity of the return light. Besides, the intensity of the return light affects the intensity of the interference light. Therefore, the stationary determination unit 262 can make the stationary determination based on a time course of the intensity of a signal from the CCD image sensor 223.

As a second example, when there is provided the front image acquisition optical system mentioned above, the stationary determination can be made in the following manner. First, a moving image of the subject's eye E is captured with the front image acquisition optical system. Thereby, front images (frames) of the subject's eye E are acquired at predetermined intervals. The stationary determination unit 262 is sequentially fed with the front images and analyzes them to detect a characteristic site of the subject's eye E. This characteristic site is, for example, the pupil (or its center) in an anterior segment image, or the optic disc (or its center), the macula (or its center), a blood vessel, or an affected area in a fundus image. Further, the stationary determination unit 262 monitors changes in the position of the characteristic site in the front images input in time series, and thereby can determine whether the subject's eye E is substantially stationary.

(Left/Right Determination Unit 263)

The left/right determination unit 263 determines whether the subject's eye E is the left eye or the right eye (left-right determination). The left-right determination is made when both the test of the left eye and the test of the right eye are performed with the ophthalmic examination apparatus 200-a. When only one of the left and right eyes is tested, for example, information that indicates the eye to be tested is the left eye or the right eye is stored in the storage 242 in advance.

Even if the test of only one eye is performed, the left-right determination may be made to prevent the other eye from being accidentally tested. That is, for example, when the left eye is set as a test object, if the subject's eye E is determined to be the right eye as a result of the left-right determination, predetermined notification information may be output. This notification information is, for example, display information displayed on the display 281 or the flat panel display 225, or sound information output from an audio output unit (not illustrated). Besides, when the measurement light contains visible components, the notification may be provided by flashing the measurement light.

Described below are examples of the left-right determination. As a first example, the left-right determination is made based on the control state of the unit driver 210A. This example is applied when the position of the optical unit 210 varies depending on whether the left eye or the right eye is tested. As described above, the optical unit 210 is moved by the unit driver 210A under the control of the main controller 241. Each time controlling the unit driver 210A, the main controller 241 sends the control contents to the left/right determination unit 263. The left/right determination unit 263 determines whether the optical unit 210 is placed in a position for the test of the left eye or a position for the test of the right eye based on the control contents received from the main controller 241. Incidentally, a range of the position for the test of the left eye and a range of the position for the test of the right eye are set in advance.

As a second example, when there is provided the front image acquisition optical system mentioned above, the left-right determination can be made by analyzing a front image. If the front image is an image of the anterior eye segment, the inner corner side and the outer corner side of the subject's eye E can be identified based on, for example, the shape of the eyelid. Thus, it is possible to determine whether the subject's eye E is the left eye or the right eye. If the front image is an image of the fundus, a determination can be made on whether the subject's eye E is the left eye or the right eye based on the position of the optic disc, the position of the macula, the positional relationship between the optic disc and the macula, the running state (distribution) of blood vessels, and the like.

Incidentally, the left-right determination function as described above may not necessarily be provided. For example, the subject or the examiner may enter that the subject's eye E is the right eye or the left eye with the operation unit 282.

The ophthalmic examination apparatus 200-a may have a configuration without the data processor 260. In this case, the main controller 241 controls the communication unit 270 to send a detection signal (detection data) from the CCD image sensor 223, data obtained by processing the detection data, or image data formed by the image forming unit 250 to the cloud server 100 as the examination data. The examination data processor 150 of the cloud server 100 performs predetermined data processing based on the data received from the ophthalmic examination apparatus 200-a.

If both the ophthalmic examination apparatus 200-a and the cloud server 100 has the data processing function, for example, predetermined data processing can be implemented by the cooperation between the examination data processor 150 and the data processor 260. As another example of processing in this case, when the cloud server 100 has a heavy processing load, the ophthalmic examination apparatus 200-a may perform the predetermined data processing. On the other hand, when having a lower processing load, the cloud server 100 may perform the predetermined data processing. The determination on the processing load is made by, for example, the arithmetic and control unit 110. The usage conditions of the plurality of the ophthalmic examination apparatuses 200-a can be taken into account in the determination on the processing load.

(Communication Unit 270)

The communication unit 270 performs data communication via the communication line N. The method of the communication is arbitrary. For example, the communication unit 270 includes a communication interface conforming to the Internet, a communication interface conforming to LAN, and a communication interface conforming to near field communication. The data communication may be wireless or wired communication. The data communication is performed with, for example, the cloud server 100, the patient terminals 300-b, and the like.

Data transmitted and received by the communication unit 270 may be encrypted. In this case, the controller 240 (or the data processor 260) includes an encrypter that encrypts data to be transmitted, and a decoder that decodes received data.

[Patient Terminal 300-*b*]

The patient terminal 300-*b* is a computer terminal that is provided for use by a patient user. Examples of the patient terminal 300-*b* include a computer terminal that a patient user owns and a computer terminal lent to a patient user. The patient terminal 300-*b* may be in a form of a mobile phone, a smart phone, a tablet computer, a laptop computer, a desktop computer, or the like. An application program is installed in the patient terminal 300-*b* for utilizing the service provided by the cloud server 100. This application program includes, for example, a general purpose browser and/or dedicated application software.

[Appointee Terminal 400-*c*]

The appointee terminal 400-*c* is a computer terminal that is provided for use by a person (appointee) allowed to use the service provided by the cloud server 100. Appointees are users other than patient users and users of the diagnostician terminals 500-*d*. Examples of the appointees include those who related to patients, medical staff other than the users of the diagnostician terminals 500-*d* or the medical staff terminals 650-*f*. Note that the medical staff is a generic name of a person engaged in medical practice. Examples of the medical staff include doctors, dentists, nurses, pharmacists, public health nurses, midwives, clinical laboratory technicians, health laboratory technicians, medical radiation technologists, medical X-ray technicians, nutritionists, national registered dietitians, physical therapists, work therapists, orthoptist, emergency medical technicians, medical accounting personnel, and the like.

Examples of the appointee terminal 400-*c* include a computer terminal that an appointee owns, a computer terminal lent to an appointee, and a computer terminal that is installed in a predetermined location (e.g., a pharmacy, an optician's store, an elderly welfare facility, a hospital, a clinic, an optometrist, etc.). The appointee terminal 400-*c* may be in a form of a mobile phone, a smart phone, a tablet computer, a laptop computer, a desktop computer, or the like. An application program is installed in the appointee terminal 400-*c* for utilizing the service provided by the cloud server 100. This application program includes, for example, a general purpose browser and/or dedicated application software.

[Diagnostician Terminal 500-*d*]

The diagnostician terminal 500-*d* is a computer terminal that is provided for use by a physician who performs the diagnosis of target diseases of the service provided by the cloud server 100 (or a person who enters the diagnostic result on a computer, collectively referred to as diagnostician and the like). Examples of the diagnostician terminal 500-*d* include a computer terminal that a diagnostician owns, a computer terminal lent to a diagnostician, and a computer terminal that is installed in a predetermined location (e.g. a hospital, a clinic, a health diagnostic center, a medical checkup center, a test car, etc.). The diagnostician terminal 500-*d* may be in a form of a mobile phone, a smart phone, a tablet computer, a laptop computer, a desktop computer, or the like. An application program is installed in the diagnostician terminal 500-*d* for utilizing the service provided by the cloud server 100. This application program includes, for example, a general purpose browser and/or dedicated application software.

The user of the diagnostician terminal 500-*d* may be the attending physician of the patient user. In this case, through the use of the diagnostician terminal 500-*d*, the attending physician creates a diagnostic report on the basis of examination data obtained by the ophthalmic examination apparatus 200-*a* and/or the analysis result thereof. The user of the diagnostician terminal 500-*d* may also be a radiologist. In this case, through the use of the diagnostician terminal 500-*d*, the radiologist creates an interpretation report based on examination data (image data) obtained by the ophthalmic examination apparatus 200-*a*. The interpretation report is sent to the diagnostician terminal 500-*d* of the attending physician. The attending physician can create a diagnostic report with reference to the interpretation report.

[Medical Institution Server 600-*e*]

The medical institution server 600-*e* is a server that is installed in a medical institution (a hospital, a clinic, etc.) allowed to use the service provided by the cloud server 100. The medical institution server 600-*e* provides the service in cooperation with the cloud server 100, and is configured to operate in conjunction with, for example, a hospital information system (including an ordering system, an electronic medical record system, image filing system, a receipt system, etc.). The medical institution server 600-*e* provides the service offered by the cloud server 100 to a plurality of clients (the medical staff terminals 650-*f*, etc.). An application program is installed in the medical institution server 600-*e* for utilizing the service provided by the cloud server 100. The application program includes, for example, dedicated application software.

[Medical Staff Terminal 650-*f*]

The medical staff terminal 650-*f* is used to utilize the service provided by the cloud server 100 through the medical institution server 600-*e*. Examples of the medical staff terminal 650-*f* include a computer terminal that medical staff owns, a computer terminal lent to medical staff, and a computer terminal that is installed in a predetermined location (a hospital, a clinic, etc.). The medical staff terminal 650-*f* may be in a form of a mobile phone, a smart phone, a tablet computer, a laptop computer, a desktop computer, or the like. An application program is installed in the medical staff terminal 650-*f* for utilizing the service provided by the cloud server 100. This application program includes, for example, a general purpose browser and/or dedicated application software. Note that the medical staff terminal 650-*f* may include the plurality of the diagnostician terminals 500-*d*.

[Financial Institution Server 700-*g*]

The financial institution server 700-*g* is a server for processing information dealt by banks, credit card companies, and the like. The financial institution server 700-*g* exchanges information related to the financial institution (e.g., information on accounting, information on the payment of fees, etc.) with the cloud server 100 regarding the service provided by the cloud server 100. An application program is installed in the financial institution server 700-*g* for utilizing the service provided by the cloud server 100. This application program includes, for example, dedicated application software.

[Insurance Provider Server 800-*h*]

The insurance provider server 800-*h* is a server for processing information dealt by public insurance agencies, insurance companies, and the like. The insurance provider server 800-*h* exchanges information related to the insurance provider (e.g., information on accounting, information on insurance benefits, etc.) with the cloud server 100 regarding the service provided by the cloud server 100. An application program is installed in the insurance provider server 800-*h* for utilizing the service provided by the cloud server 100. This application program includes, for example, dedicated application software.

[Examination Data Processing Apparatus 900]

The examination data processing apparatus 900 may be used to, for example, perform an analysis process that cannot be implemented by the cloud server 100, the ophthalmic examination apparatus 200-*a*, and the like. The analysis process may be optional, and may be a service that incurs additional fees. The analysis process performed by the examination data processing apparatus 900 is determined arbitrarily.

The analysis process performed by the examination data processing apparatus 900 may include an analysis process of the same type as and more accurate and/or reliable than the analysis process performed by the cloud server 100. For example, by utilizing a clinical database obtained for a number of eyes (big data), it is possible to perform an analysis process of the same type as that performed by the cloud server 100 or the like. The big data may be updated periodically or non-periodically to include new clinical data.

Further, the analysis process performed by the examination data processing apparatus 900 may include an analysis process of different type from the analysis process performed by the cloud server 100, the ophthalmic examination apparatus 200-*a*, and the like.

For example, the examination data processing apparatus 900 may perform the analysis processing on the basis of an order from a patient user or physician. This order is, for example, optionally entered for each test. Alternatively, the order is automatically made for a patient user and/or a test type set in advance.

[Usage Modes]

Described below are the usages of the ophthalmic information system 1 of the embodiment. In the following, a description is given of various types of phases of the services provided by the ophthalmic information system 1, and various forms of the services. In actual operation, it is possible to selectively apply one or more of a plurality of the usage modes described below. Alternatively, in actual operation, it may be possible to provide services different from any of the following usage modes. It should be noted that such services are within the scope of the present invention.

[Overview]

Figure 5:
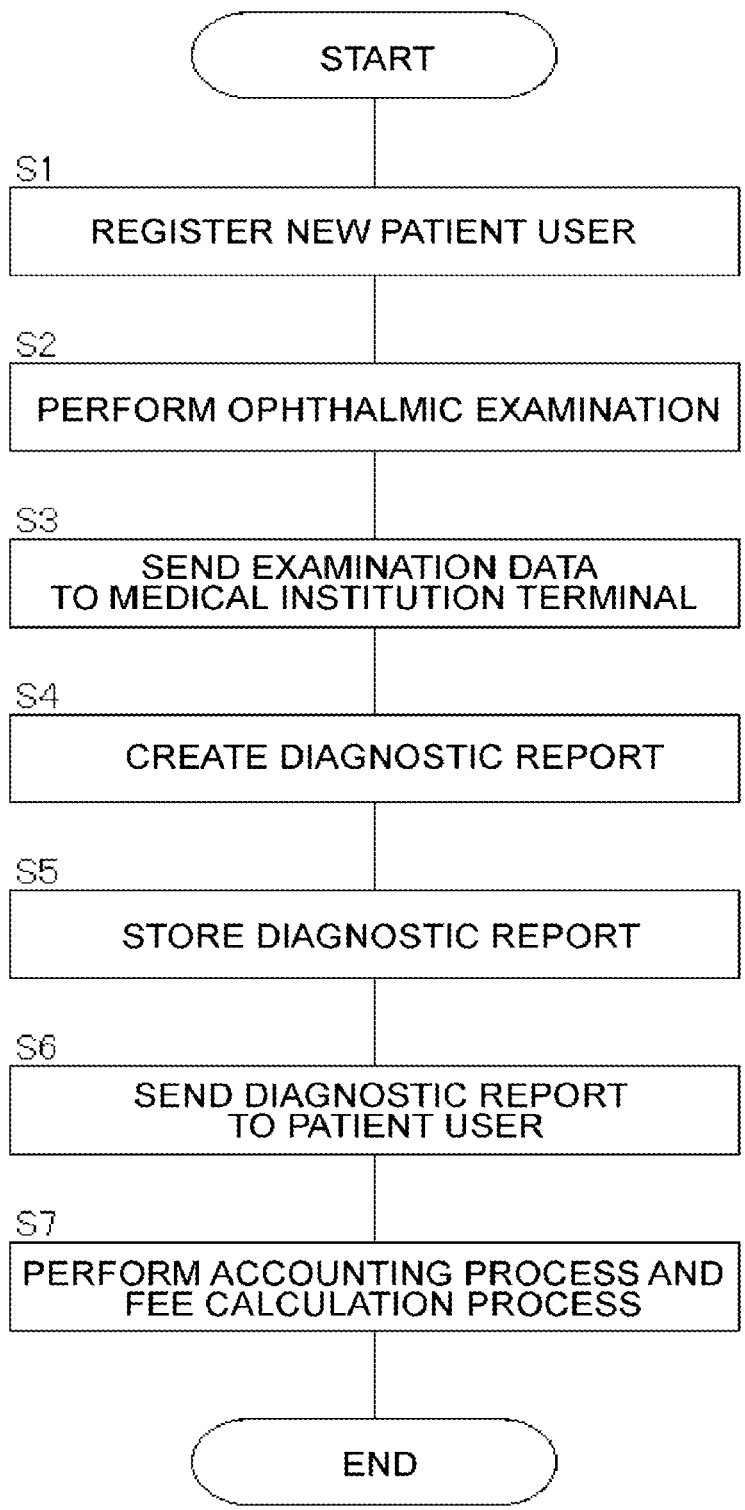
FIG. 5 is a flowchart illustrating an example of the usage mode of a system according to an embodiment.

First, an overview of the usage mode is described. FIG. 5 illustrates the entire flow of the usage mode as an example.

(S1: Register Patient User)

A process related to the usage mode is performed with respect to each patient user. As the first step in the process for each patient user, the user is registered to the service provided by the ophthalmic information system 1. The registration of a new patient user is carried out, for example, in response to diagnosis by a doctor. Specifically, when diagnosing that a patient has a predetermined disease (a disease that is treated in the service, such as age-related macular degeneration, diabetic retinopathy, and glaucoma), or diagnosing that a patient may have a predetermined disease, the doctor introduces the service to the patient. Incidentally, subscription to the service is optional.

Having determined to subscribe the service, the patient enters required information such as patient information, disease name, and information related to a financial institution and an insurance provider that he/she has contract with. For example, the patient can make the entry on web or by filling out a predetermined form. The information entered by the patient is fed to the cloud server 100 manually or automatically.

The arithmetic and control unit 110 sends the received information to the patient information management unit 141. The patient information management unit 141 registers the patient as a user based on the information. The user registration process includes the issuance of a patient user ID, the creation of a patient user account, and the storage of information in this account (the patient information storage area 121). Once user registration is complete, the cloud server 100 performs a process for sending information about the completion of registration to the new patient user. The information is sent to the new patient user by, for example, sending e-mail to the patient terminal 300-*b* of the patient user (and/or the appointee terminal 400-*c* of a person related to the patient user), making a call to a mobile phone and/or a fixed phone, sending a facsimile, and writing and sending a postcard or a letter.

Incidentally, at least part of information required to subscribe the service may be provided from the medical institution server 600-*e* to the cloud server 100.

(S2: Perform Ophthalmic Examination)

The patient user is provided with information indicating the location where the ophthalmic examination apparatus 200-*a* is installed. As an example of this process, the cloud server 100 sends a list or a map that represents the location(s) of the ophthalmic examination apparatus(es) 200-*a* to the patient terminal 300-*b*. Alternatively, the patient user is provided with a list or a map printed out by the cloud server 100.

The ophthalmic examination apparatus 200-*a* to be described in the list or the map may be selected from the location of the patient user. For example, based on the address of the patient user, the patient information management unit 141 selects those present within a predetermined range with respect to the address (distance, way, time, area, etc.) from all of the ophthalmic examination apparatuses 200-*a*. The arithmetic and control unit 110 creates a list or a map that represents the location(s) of the ophthalmic examination apparatus(es) 200-*a* selected, and sends the list or the map to the patient terminal 300-*b* of the patient user by controlling the communication unit 130.

In a manner as described above, the patient user can know the location(s) of the ophthalmic examination apparatus(es) 200-*a*. The patient user visits a desired location at a desired or predetermined timing, and has a test using the ophthalmic examination apparatus 200-*a*. This test is conducted by a trained person or the patient user himself/herself. Before taking a test, the patient user enters his/her user ID. The ophthalmic examination apparatus 200-*a* carries out the test of the eye of the patient user to generate examination data. Then, the ophthalmic examination apparatus 200-*a* sends the examination data and the patient user ID to the cloud server 100.

The patient information management unit 141 of the cloud server 100 searches for the account of the patient user based on the patient user ID received from the ophthalmic examination apparatus 200-*a*. The patient information management unit 141 stores the examination data in the account searched. Besides, the patient information management unit 141 adds the content (examination date and time, test type, etc.) of this test to examination history in the account.

Further, the patient information management unit 141 determines whether analysis is required based on default information related to the patient user or a request entered for this test. If analysis is required, the patient information management unit 141 sends the patient user ID, the examination data (and past medical information: the same applies hereinafter), and an analysis type to the arithmetic and control unit 110. The arithmetic and control unit 110 sends the patient user ID, the examination data, and the analysis type to an analyzer (the examination data processor 150 or the examination data processing apparatus 900) based on the analysis type. Having received the information, the analyzer performs an analysis process based on the examination data, and sends the analysis result obtained thereby to the arithmetic and control unit 110 with the patient user ID. The arithmetic and control unit 110 stores the analysis result in the account of the patient user, and adds the content of this analysis to examination history.

(S3: Send Examination Data to Medical Institution Terminal)

Subsequently, the patient information management unit 141 specifies a medical institution terminal (the diagnostician terminal 500-*d* or the medical institution server 600-*e* (and the medical staff terminal 650-*f*)) as the destination of the examination data and the like based on the identification information of the medical institution recorded in the account of the patient user (and patient ID in the medical institution). The arithmetic and control unit 110 sends the examination data, the analysis result, and the like obtained in step S2 to the medical institution terminal thus specified together with the patient user ID. The medical institution terminal as the destination is, for example, a computer terminal used by the doctor who made the diagnosis for the patient user in step S1.

(S4: Create Diagnostic Report)

Having received the examination data and the like, the doctor creates a diagnostic report. The medical institution terminal is equipped with a user interface for creating reports based on examination data (including the analysis result). The user interface may include software for providing report writing tools (display screen, software keys, etc.) as well as hardware such as a display device and an operation device. The medical institution terminal sends the diagnostic report thus created to the cloud server 100 with the patient user ID.

(S5: Store Diagnostic Report)

The patient information management unit 141 of the cloud server 100 searches for the account of the patient user based on this patient user ID, and stores the diagnostic report in the account searched.

(S6: Send Diagnostic Report to Patient User)

The arithmetic and control unit 110 performs a process for sending the diagnostic report to the patient user. As an example of this process, email enclosing the diagnostic report is sent to the patient terminal 300-*b* and/or the appointee terminal 400-*c*. As another example, as described above, the diagnostic report may be sent by facsimile, post card, letter, or the like.

(S7: Accounting Process and Fee Calculation Process)

The accounting processor 170 performs accounting process for the patient user, and calculation process of the amount of fees for predetermined users in a manner, for example, mentioned above.

The patient information management unit 141 records information related to the accounting (service use date and time, breakdown of the service, amount of a fee to be charged, etc.) in the account of the patient user. Similarly, the financial institution information management unit 144 and/or the insurance provider information management unit 145 record(s) information related to the accounting and information related to the patient user in the corresponding account(s). The information related to the accounting thus recorded is aggregated at a predetermined timing and sent to the user.

In addition, the user information management unit 140 records information related to fees (information related to the patient user, service use date and time, breakdown of the service, breakdown of the fee, amount of the fee, etc.) in the account of a user to receive the fee (medical institution, examination apparatus installation institution, etc.). The information related to fees thus recorded is aggregated at a predetermined timing and sent to the user.

The above is the entire flow of the usage mode as an example. In the following, a description is given of examples of processes performed in several stages in the exemplary usage mode.

[Process Related to Visit Request]

There is a case that the diagnostic report contains a visit request. The visit request is a request from the doctor for a patient user to have medical practice in a medical institution. The visit request occurs when, for example, a doctor determines that a hospital visit is required based on the examination data, analysis result, and the like, when the next visit time is coming in a case in which regular visits are required. For example, as described above, the visit request includes at least information indicating the necessity of a hospital visit (character string information, presence or absence of a check mark, etc.). The visit request may further include scheduled visit date and time.

Figure 6A:
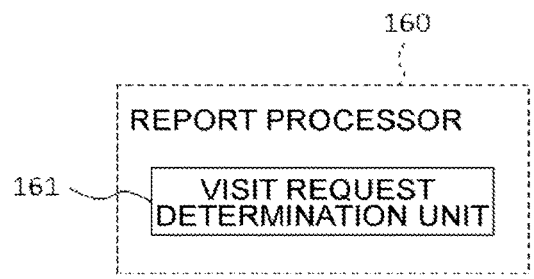
FIG. 6A is a schematic diagram illustrating an example of the configuration of a cloud server according to an embodiment.

If the process related to the visit request is applied, the report processor 160 of the cloud server 100 includes a visit request determination unit 161 (see FIG. 6A). The visit request determination unit 161 determines whether the diagnostic report includes a visit request for the patient user. The visit request determination unit 161 determines on the necessity of a hospital visit based on information filled in a visit request entry column in the diagnostic report. If visit date and time have been entered, the visit request determination unit 161 recognizes the visit date and time. On the other hand, the patient information management unit 141 may be configured to exchange information with the patient user (the patient terminal 300-*b* and/or the appointee terminal 400-*c*) to set the visit date and time when visit date and time have not been entered.

Figure 6B:
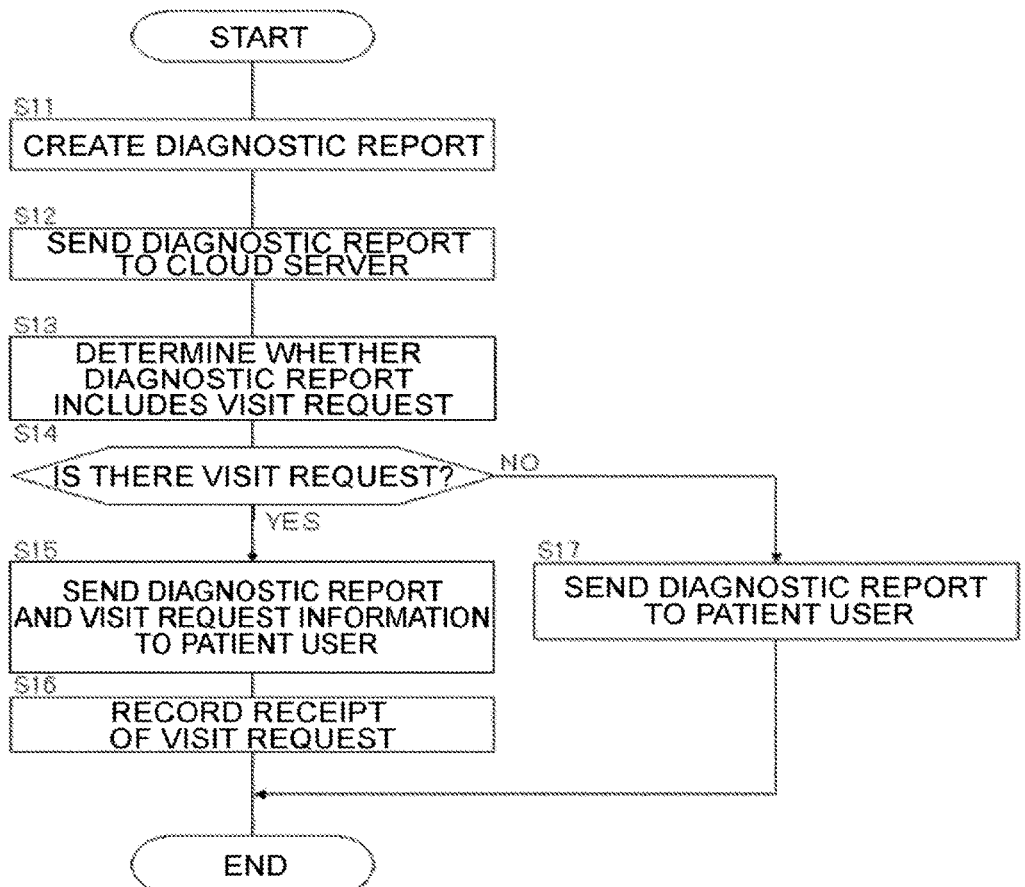
FIG. 6B is a flowchart illustrating an example of the usage mode of a system according to an embodiment.

FIG. 6B illustrates an example of the process related to the visit request. A diagnostic report created in the same manner as step S4 in FIG. 5 is sent to the cloud server 100 (S11, S12). The visit request determination unit 161 determines whether the diagnostic report includes a visit request for the patient user (S13).

If the diagnostic report includes a visit request (S14: YES), the arithmetic and control unit 110 performs a process for sending the diagnostic report and visit request information to the patient user (S15). As this process, e-mail is sent to the patient terminal 300-*b* and/or the appointee terminal 400-*c* with attachment information. The visit request information may include, for example, a message for prompting the patient user to make a visit (regular visit) to a hospital, information related to a corresponding medical institution and doctor, and scheduled visit date and time. If the information includes visit date and time, it may further include information for a reply as to whether it is possible to visit on the scheduled visit date and time. For example, the patient user notifies the cloud server 100 of whether he/she can visit a hospital on the scheduled visit date and time by manipulating the patient terminal 300-*b*. The arithmetic and control unit 110 sends the content of the notification to the diagnostician terminal 500-*d* or the medical institution server 600-*e*. In addition, the patient information management unit 141 records the receipt of a visit request and the content of the notification with respect to the visit request in the account of the patient user (S16).

If the diagnostic report does not include a visit request (S14: NO), the arithmetic and control unit 110 performs a process for sending the diagnostic report to the patient user as in step 6 in FIG. 5 (S17). A message indicating that there is no visit request may be sent to the patient user together with the diagnostic report. This is the end of the process related to the visit request described as an example.

[Process Related to Examination Request]

The ophthalmic information system 1 can perform a process for requesting a test of the patient user. The examination request process is performed for, for example, patient users with low frequency of testing. Described below is an example of the examination request process.

Figure 7A:
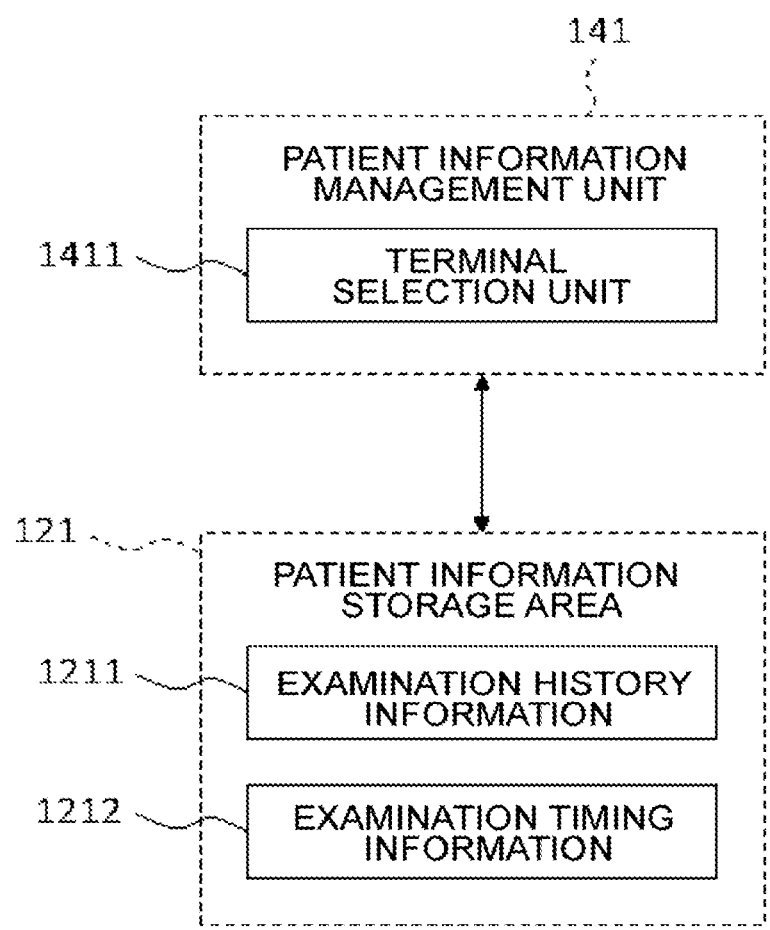
FIG. 7A is a schematic diagram illustrating an example of the configuration of a cloud server according to an embodiment.

FIG. 7A illustrates an example of a configuration for the case where examination request process is applied. In the patient information storage area 121, examination history information 1211 and examination timing information 1212 are stored. The examination history information 1211 is, as described above, information stored in the account of each patient user, and includes the content (examination date and time, test type, etc.) of test conducted in the past. The examination timing information 1212 indicates desired timing for carrying out test. The examination timing information 1212 includes, for example, interval of examinations, test schedule (dates), or the like. In this example, the examination timing information 1212 is provided for each patient user, but is not limited thereto. For example, the examination timing information 1212 may be provided for each attribute, such as a disease and a drug used. In this embodiment, a detailed description is given of an example in which the examination timing information 1212, including interval of examinations, is provided for each patient user; however, a similar process can be performed when the examination timing information 1212 has another configuration.

The patient information management unit 141 is provided with a terminal selection unit 1411. The terminal selection unit 1411 selects one or more of patient terminals (the patient terminals 300-*b* and/or the appointee terminals 400-*c*) based on the examination timing information 1212. In particular, in this embodiment, the terminal selection unit 1411 selects a patient terminal based on the interval of examinations and the latest examination date stored in the patient information storage area 121. The latest examination date corresponds to the latest one of the examination dates and times recorded in the examination history information 1211. The interval of examinations is included in the examination timing information 1212.

For example, the terminal selection unit 1411 performs the above process for a patient user designated in advance. In this case, the selection of a patient terminal is equivalent to the determination of whether an examination request is to be made to the patient user. In another example, the terminal selection unit 1411 performs the above process for a plurality of patient users at a predetermined timing, thus specifying a patient user(s) (patient terminal(s)) to be notified of the examination request.

Described below is a specific example of the process performed by the terminal selection unit 1411. It is assumed that "30 days" is recorded in the examination timing information 1212 as the interval of examinations. It is also assumed that "Mar. 1, 2014" is recorded in the examination history information 1211 as the latest examination date. The terminal selection unit 1411 adds the interval of examinations "30 days" to the latest examination date "2014 Mar. 1". Thereby, "Mar. 31, 2014" is obtained. This day is hereinafter referred to as "calculation date".

The terminal selection unit 1411 compares the calculation date "Mar. 31, 2014" with a predetermined date. The predetermined date is set arbitrarily. For example, the predetermined date may be the current date (the day on which the terminal selection unit 1411 performs the process), or it may be another date. As an example of the latter, a day before the current date can be set. The retroactive time period may be set in consideration of, for example, the time period considered necessary from the notification of examination request to the implementation of test.

When the calculation date is the same as the predetermined date or earlier than it, the terminal selection unit 1411 determines that the patient user is to be notified of the examination request. In contrast, when the calculation date is later than the predetermined date, the terminal selection unit 1411 determines that the patient user is not to be notified of the examination request. A specific example is described below. If the current date (predetermined date) is "Apr. 1, 2014", the calculation date "Mar. 31, 2014" is prior to the current date "Apr. 1, 2014". The calculation date "Mar. 31, 2014" corresponds to the final day of the time period during which the patient user should take an examination first after the latest examination date "Mar. 1, 2014" recorded in the examination history information 1211. The fact that the final day is the same as or earlier than the current date "Apr. 1, 2014" means that the patient user has not taken the examination until the current date, which is (after) the final day of the period in which the patient user should take the examination. Therefore, the patient user is to be notified of the examination request. On the other hand, if the current date (predetermined date) is "Mar. 15, 2014", the calculation date "Mar. 31, 2014" is later than the current date "Mar. 15, 2014". In other words, the final day of the period, in which the patient user should take the examination, has not yet arrived. In this case, the patient user is not to be notified of the examination request.

Figure 7B:
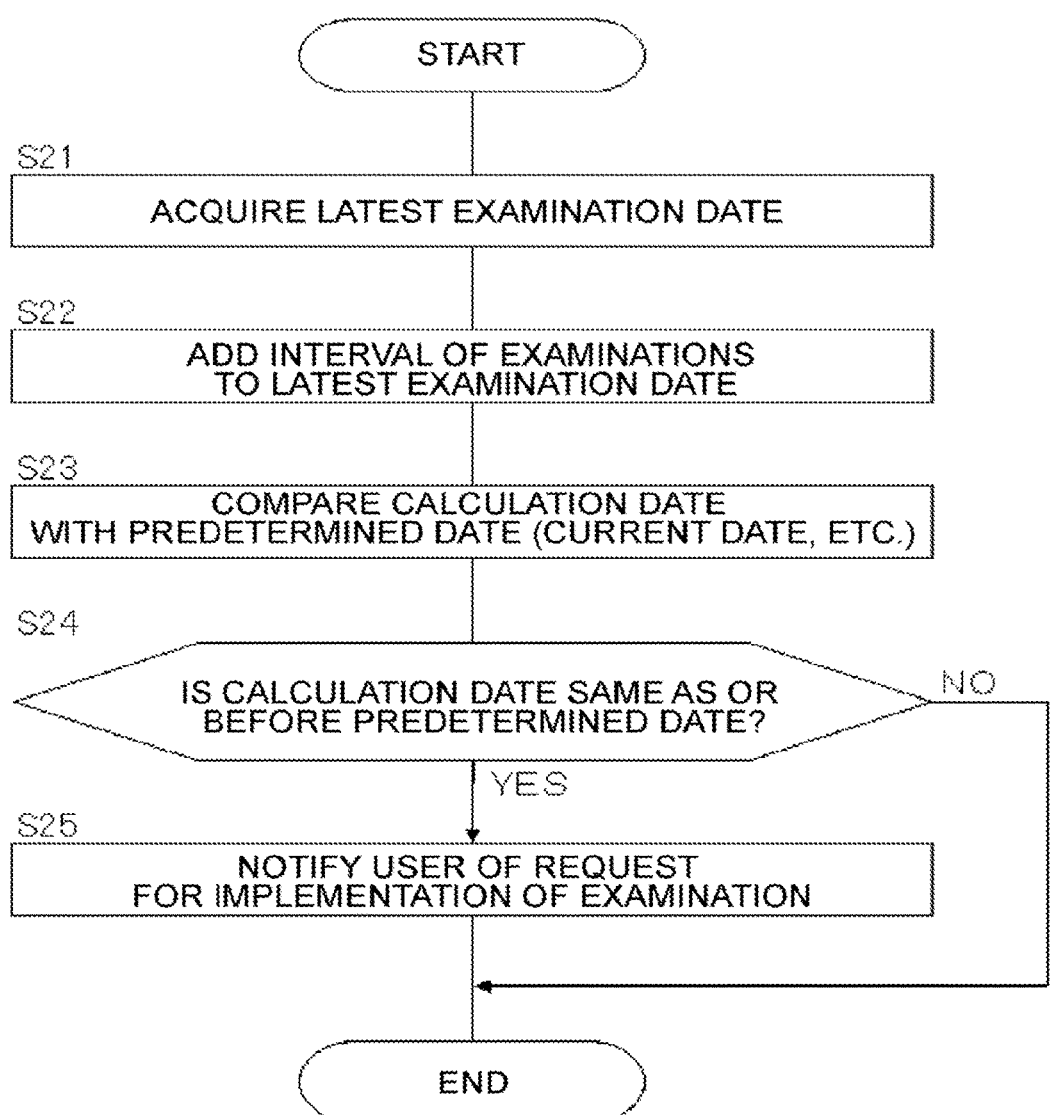
FIG. 7B is a flowchart illustrating an example of the usage mode of a system according to an embodiment.

FIG. 7B illustrates an example of the process related to the examination request. The examination history information 1211 and the examination timing information 1212 are stored in advance. The arithmetic and control unit 110 starts the operation of the terminal selection unit 1411 at a predetermined timing. The terminal selection unit 1411 acquires the latest examination date with reference to the examination history information 1211 (S21). Then, the terminal selection unit 1411 adds the interval of examinations recorded in the examination timing information 1212 to the latest examination date acquired (S22). Subsequently, the terminal selection unit 1411 compares the calculation date obtained by the addition with a predetermined date (current date, etc.) (S23).

If the calculation date is later than the predetermined date (S24: NO), it is determined that the patient user is not to be notified of the examination request. Thus, the process related to the patient user ends.

On the other hand, if the calculation date is the same as or before the predetermined date (S24: YES), the patient user is determined to be notified of the examination request. If this determination result is obtained, the patient information management unit 141 retrieves the address of the patient terminal of the patient user (the patient terminal 300-*b* and/or the appointee terminal 400-*c*) from the account of the patient user. The arithmetic and control unit 110 controls the communication unit 130 to send information (examination request) for requesting implementation of an examination to the patient terminal to which the address obtained by the patient information management unit 141 is assigned (S 25). The examination request includes, for example, a message prompting the implementation of an examination, and a date by which the examination should be completed. The examination request may include the location of the ophthalmic examination apparatus 200-*a* determined from the location of the patient user.

Incidentally, the patient user may be notified of the examination request through a communication means such as facsimile, post card, letter, or the like. This is the end of the process related to the examination request described as an example.

[Process of Notifying Location of Ophthalmic Examination Apparatus]

The ophthalmic information system 1 can perform a process of notifying the patient user of the location of the ophthalmic examination apparatus 200-*a*. This process is useful to provide information about the ophthalmic examination apparatus 200-*a* in the neighborhood of the place where the patient user is staying when, for example, he/she is staying in a location other than the usual location (home, etc.) (e.g., during a travel). This process is also effective when the patient user has moved. Described below is a process of this example.

FIG. 8A illustrates an example of a configuration for the case where the process of this example is applied. Patient location information 1213 is stored in the patient information storage area 121. The patient location information 1213 indicates the location of the patient user. The patient location information 1213 may include information entered in advance by the patient user or the like (the location of home or the like, travel schedule, etc.). The patient location information 1213 may include information obtained substantially in real time. The information obtained substantially in real time refers to information indicating the place, region, or the like where the patient user is currently staying. This information is provided by, for example, a current location positioning function (navigation satellite system, etc.) installed in the patient terminal 300-*b*.

The name of an institution where the ophthalmic examination apparatus 200-*a* is installed (pharmacy name, glasses shop name, etc.), and contact information (location, telephone number, e-mail address, IP address, name of a person in charge, etc.) are stored in the examination apparatus information storage area 123. In particular, the location of the examination apparatus installation institution is stored as apparatus location information 1231. The examination apparatus information management unit 143 of the user information management unit 140 is provided with an examination apparatus selection unit 1431. The examination apparatus selection unit 1431 selects one or more of the ophthalmic examination apparatuses 200-*a* based on the location of a certain patient user and the apparatus location information 1231. A specific example of this process is described later.

Figure 8B:
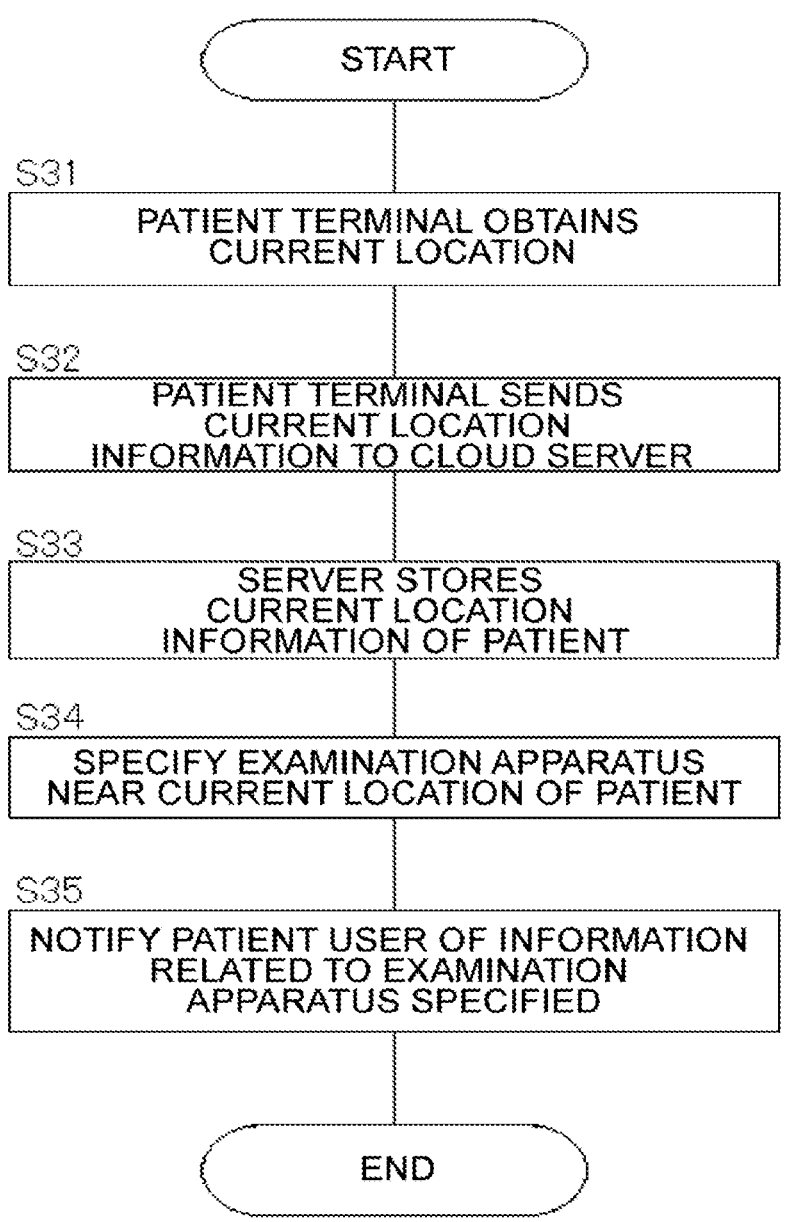
FIG. 8B is a flowchart illustrating an example of the usage mode of a system according to an embodiment.

FIG. 8B illustrates an example of the process for notifying the patient user of the location of the ophthalmic examination apparatus. A certain patient user is considered. The patient terminal 300-*b* of this patient user (or the appointee terminal 400-*c*) obtains the current location thereof by a navigation satellite system such as the Global Positioning System (GPS) (S31). The current location is considered to be the place where the patient user is at the present. The patient terminal 300-*b* sends information indicating the current location (current location information) to the cloud server 100 together with the patient user ID (S 32). The patient information management unit 141 searches for an account corresponding to the patient user ID sent from the patient terminal 300-*b*, and stores the current location information in the account (S33). The information thus stored is used as the patient location information 1213.

The patient information management unit 141 sends the current location information recorded in the patient location information 1213 to the examination apparatus information management unit 143. The examination apparatus selection unit 1431 selects one or more of the ophthalmic examination apparatuses 200-*a* under its management based on the current location information and the apparatus location information 1231. This process is carried out by, for example, specifying the ophthalmic examination apparatus 200-*a*, which is installed in a predetermined range (distance, way, time, area, etc.) with respect to the current location of the patient user (S 34).

The user information management unit 140 sends information related to the ophthalmic examination apparatus 200-*a* specified by the examination apparatus selection unit 1431 to the arithmetic and control unit 110. This information (specified examination apparatus information) includes, for example, the name of an institution where the ophthalmic examination apparatus 200-*a* is installed (pharmacy name, glasses shop name, etc.), and contact information (address, phone number, etc.) of the institution. The arithmetic and control unit 110 notifies the patient user of the specified examination apparatus information (S35). This notification process is performed by, for example, sending an e-mail to the patient terminal 300-*b* of the patient user and/or the appointee terminal 400-*c*. This is the end of the process for notifying the patient user of the location of the ophthalmic examination apparatus described as an example.

[Accounting Process and Fee Calculation Process]

As described above, the accounting processor 170 of the cloud server 100 performs the accounting process and the fee calculation process. The accounting process is performed when a user uses a service set in advance to charge the use fee to the user. The fee calculation process is performed when one user provides a predetermined service to another user to determine a fee to be received by the user who has provided the service. Described below is an example of a process performed in the accounting process and the fee calculation process.

When a charge occurs, the accounting processor 170 performs the accounting process for a predetermined user and the fee calculation process for one or more other users based on the amount to be charged and the fee calculation rule 126. As an example, when a diagnostic report is sent to the patient terminal 300-*b* or the like, the accounting processor 170 calculates fees for each of: the medical institution (or the doctor) that has created the diagnostic report; the installation institution (pharmacy, optician's store, etc.) where the ophthalmic examination apparatus 200-*a*, which has conducted the examination used to create the diagnostic report, is installed; and the administering authority of the ophthalmic information system 1. The fee to the medical institution occurs for medical practice including the creation of the diagnostic report. The fee to the examination apparatus installation institution occurs for the fact that the ophthalmic examination apparatus 200-*a* is installed. The fee to the system administering authority occurs for the use of the system. Those that receive fees are not limited to the above. For example, if the examination data processing apparatus 900 is used, a fee is generated for an institution that operates the examination data processing apparatus 900. In addition, if an optional service is provided, a fee occurs for a provider of the optional service.

The ophthalmic information system 1 may be configured to manage fees for medical institutions by the account of each of the medical institutions. In this case, the storage 120 of the cloud server 100 is provided with an account corresponding to each medical institution user (the medical institution information storage area 122). The medical institution information storage area 122 is associated with a user ID (medical institution ID, medical institution identification information) of the corresponding medical institution user.

When the amount of fees has been calculated by the accounting processor 170, if those that receive the fees include a medical institution, the arithmetic and control unit 110 sends the user ID of the medical institution and fee information thereof to the medical institution information management unit 142. The medical institution information management unit 142 searches for the account associated with the medical institution ID, and stores the fee information in this account. The fee information includes, for example, the amount of the fee, the type of the service for which the fee has occurred, the date and time on which the service was provided, identification information of the billing subscriber (patient user ID, etc.).

In the manner described above, fee information is accumulated in the account of each medical institution user. The medical institution information management unit 142 aggregates the fee information accumulated in the account of each medical institution user. The corresponding medical institution user is notified of the fee information thus aggregated. This notification process includes, for example, a process of sending aggregated data to the medical institution server 600-*e* by the arithmetic and control unit 110. Instead of the aggregating process as described above, the transmission of the fee information may be carried out each time a payment occurs. Further, when two or more medical institutions form a group, the fee information may be aggregated with respect to these medical institutions.

Although the use fee (amount to be charged) of the ophthalmic information system 1 is, in effect, charged to the user who has used a corresponding service, there is also a case where a user other than the user is notified of the fees to be charged. For example, if the patient user has subscribed to an insurance policy, the amount to be charged for the use of a service by the patient user may be sent to the insurance provider. Described below is an example of the process performed in such a case.

As illustrated in FIG. 1, the cloud server 100 can communicate with the insurance provider server 800-*h* of each insurance provider user via the communication line N. The storage 120 of the cloud server 100 is provided with the account of each insurance provider user (the insurance provider information storage area 125). The insurance provider information management unit 145 manages each of the accounts. Each account stores the user ID of each patient user who subscribes to an insurance policy. Similarly, the account of each patient user stores the user ID of an insurance provider to which the patient user subscribes. The information that associates the patient user ID and the insurance provider user ID is not limited to this. For example, the information that associates the patient user IDs and the insurance provider user IDs can be provided independently.

When a charge to a patient user occurs, the patient information management unit 141 or the insurance provider information management unit 145 specifies an insurance provider user ID associated with the user ID of the patient user with reference to the association information described above. The insurance provider information management unit 145 retrieves the address of the insurance provider server 800-*h* of the insurance provider user from the account associated with the insurance provider user ID specified. In addition, the insurance provider information management unit 145 stores information related to the patient user (patient user ID, etc.), and information related to this accounting (amount to be charged, service provision date, etc.) in the account of the insurance provider user.

The arithmetic and control unit 110 controls the communication unit 130 to transmit information related to the accounting (accounting information) to the insurance provider server 800-*h* to which the address retrieved by the insurance provider information management unit 145 is assigned. This transmission process is performed by, for example, sending the accounting information aggregated by the insurance provider information management unit 145 at a predetermined timing. Alternatively, the transmission process may be performed every time a charge occurs.

While a description has been given of the case where accounting information is sent to the insurance provider, the accounting information may be sent to financial institution users such as a bank, a credit card company, or the like. This process may be performed similarly by means of the patient information storage area 121, the financial institution information storage area 124, the patient information management unit 141, the financial institution information management unit 144, the arithmetic and control unit 110, the communication unit 130, the financial institution server 700-*g*, and the like.

[Effects]

A description is given of effects of an ophthalmic information system according to an exemplary embodiment.

According to an embodiment, the ophthalmic information system includes a server, a plurality of medical institution terminals, a plurality of ophthalmic examination apparatuses, and a plurality of patient terminals. Each of the medical institution terminals, each of the ophthalmic examination apparatuses and each of the patient terminals can communicate with the server via a communication line.

In the above example, the server corresponds to the cloud server 100, the medical institution terminals correspond to the diagnostician terminals 500-*d* and/or the medical staff terminals 650-*f*, the ophthalmic examination apparatuses correspond to the ophthalmic examination apparatuses 200-*a*, the patient terminals correspond to the patient terminals 300-*b* and/or the appointee terminals 400-*c*.

The ophthalmic examination apparatuses are installed in facilities different from the medical institutions. Examples of the facilities include a pharmacy, an optician's store, an optometrist, a welfare facility for the aged, and the like. The ophthalmic examination apparatuses each include a first communication unit, a receiving unit, an examination unit, and a first controller.

The first communication unit has a function of communication via a communication line. In the above example, the first communication unit corresponds to the communication unit 270.

The receiving unit has a function of receiving patient identification information (patient user ID). In the above example, the receiving unit corresponds to the user interface 280. Incidentally, the receiving unit may be a reader for reading the patient user ID and the like from a recording medium.

The examination unit has a function of generating examination data by optically examining an eye. In the above example, the examination unit corresponds to the optical unit 210, the image forming unit 250, and the examination data generating unit 261.

The first controller is configured to associate the examination data generated by the examination unit and the patient identification information received by the receiving unit with each other. The first controller is further configured to control the first communication unit to send, to the server, the patient identification information and the examination data associated with each other. In the above example, the first controller corresponds to the controller 240.

The medical institution terminals are used in medical institutions. The medical institution terminals each include a second communication unit, a user interface, and a second controller.

The second communication unit has a function of communication via a communication line.

The user interface is used to create a report based on the examination data generated by an ophthalmic examination apparatus. The user interface may be provided in any form. For example, the user interface may be provided as a desktop application, a web application, or a cloud application. The user interface includes, for example: a display configured to display various types of medical information including the examination data, analysis result thereof, and the like; and an operation unit (input unit) used for input operations to create a report.

The second controller is configured to control the second communication unit to send the report created by using the user interface to the server. In the above example, the report is sent directly from one of the diagnostician terminals 500-*d* to the cloud server 100, or, from one of the medical staff terminals 650-*f* to the cloud server 100 via the corresponding medical institution servers 600-*e*.

The server includes a third communication unit, a storage, a data processor, and a third controller.

The third communication unit has a function of communication via a communication line. In the above example, the third communication unit corresponds to the communication unit 130.

The storage includes a plurality of patient information storage areas each associated with patient identification information corresponding to one of a plurality of patients (patient users). The storage stores, in advance, first association information in which the patient identification information is associated with medical institution identification information (medical institution user ID) of one or more of a plurality of medical institutions. In the above example, the storage corresponds to the storage 120, and the patient information storage area corresponds to the patient information storage area 121. Besides, the first association information is stored in, for example, the account (the patient information storage area 121) of each patient user. Alternatively, the first association information may be independent information in which information related to a plurality of patients (patient user IDs, etc.) and information related to a plurality of medical institutions (medical institution user IDs) are associated with one another. Incidentally, the medical institution identification information conceptually includes identification information assigned to an individual doctor (doctor user ID).

When the third communication unit receives the patient identification information and the examination data from an ophthalmic examination apparatus, the data processor specifies one or more of the medical institution terminals corresponding to the patient identification information. This specification process is performed by referring to the first association information. In the example above, the specification process is performed by the user information management unit 140 or the like.

The third controller is configured to control the third communication unit to send the patient identification information and the examination data sent to the server from the ophthalmic examination apparatus to the medical institution terminal specified by the data processor. Further, when the third communication unit receives the patient identification information and the report from the medical institution terminal, the third controller performs at least two processes described in the following. As a first process, the third controller stores at least part of the report in the patient information storage area associated with the patient identification information. As a second process, the third controller controls the third communication unit to send at least part of the report to one or more of the patient terminals corresponding to the patient identification information. Note that the information stored in the patient information storage area in the first process may be the same as or different from the information sent to the patient terminal in the second process. In the above example, the third controller corresponds to the arithmetic and control unit 110 (and the user information management unit 140).

According to the ophthalmic information system having such a configuration, an eye examination can be conducted in a facility other than medical institutions such as a pharmacy and an optometrist, a doctor can create a report based on the examination data obtained thereby, and the report may be provided to the patient. With this, the patient can obtain a diagnostic result by simply having an examination in a facility in the neighboring location. Further, by teaching an employee of the pharmacy or the like how to operate the ophthalmic examination apparatus, the examination can be conducted smoothly. Therefore, an examination can be more readily carried out on a regular basis as compared to before for a disease that requires long-term pathology management. Thus, the ophthalmic information system of the embodiment can provide a new technology that enables suitable long-term pathology management.

In the ophthalmic information system according to the embodiment, the data processor of the server may include a determination unit configured to determine whether the report received by the third communication unit contains a visit request for the patient. Further, the third controller may be configured to perform different processes for when the report contains a visit request and when the report contains no visit request. Incidentally, in the above example, the determination unit corresponds to the visit request determination unit 161. With this configuration, a suitable process can be provided depending on the presence or absence of the visit request.

The third controller may be configured to perform the following process when it is determined that the report contains a visit request. First, the third controller specifies the medical institution identification information associated with the patient identification information of the patient with reference to the first association information. Then, the third controller controls the third communication unit to send information that requests a visit to a medical institution corresponding to the medical institution identification information specified to the patient terminal corresponding to the patient identification information. With this configuration, when the report contains a visit request, a relevant patient can be notified of this. The patient can realize that he/she is required to have medical treatment in the medical institution through this notification.

If it is determined that the report contains a visit request, the third controller may be configured to store a determination result obtained by the determination unit (presence of a visit request) in the patient information storage area associated with the patient identification information of the patient. In addition, although it is optional, a similar process may be performed (process of storing information indicating the absence of a visit request) if the report contains no visit request. With this configuration, by storing the presence or absence of a visit request, it is possible to grasp the state of hospital visits and patient's conditions.

The ophthalmic information system of the embodiment may be configured as follows. First, examination timing information indicating timing for conducting an examination is stored in advance in the storage of the server. The data processor includes a first selection unit configured to select one or more of the patient terminals based on the examination timing information. The third controller is configured to control the third communication unit to send information requesting the implementation of an examination to the patient terminal selected. Incidentally, in the above example, the first selection unit corresponds to the terminal selection unit 1411. The examination requested in this example may be performed in a non-medical institution (i.e., may be performed by any of the ophthalmic examination apparatuses), or it may be performed in a medical institution. With this configuration, it is possible to instruct the patient to conduct an examination in a suitable timing. Thus, it is possible to suitably perform long-term management of patient's conditions.

This configuration may be embodied as follows. In this example, the examination timing information includes information indicating the interval between examinations. When the third communication unit receives patient identification information and examination data from any of the ophthalmic examination apparatuses, the third controller stores examination date, which indicates the date on which the examination data is acquired, in one of the patient information storage areas associated with the patient identification information. Thereby, examination history is managed for each patient. The first selection unit is configured to select a patient terminal(s) based on the most recent examination date stored in the patient information storage area, and on the interval of examinations contained in the examination timing information. With this configuration, it is possible to selectively request a patient who has not had an examination at appropriate time intervals to undergo an examination.

The ophthalmic information system of the embodiment may be configured as follows. First, the storage of the server stores, in advance, apparatus location information indicating the location of each of the ophthalmic examination apparatuses. The third controller is configured to store the patient location information indicating the location of a patient in corresponding one of the patient information storage areas. The patient location information is, for example, input to the server automatically by a navigation satellite system or the like. Alternatively, the patient location information may be input to the server manually by the patient or a person related to him/her. The data processor includes a second selection unit configured to select one or more of the ophthalmic examination apparatuses based on the apparatus location information and the patient location information of the patient. Such a selection process may be performed using, for example, distance, way, travel time, area, or the like as a reference. The third controller is configured to control the third communication unit to send information indicating the location of the ophthalmic examination apparatus selected by the second selection unit to the patient terminal corresponding to the patient. With this configuration, it is possible to provide the location of an ophthalmic examination apparatus that can be easily accessed to the patient. Thus, the burden of the patient required for the examination can be reduced. Note that, in the above example, the second selection unit corresponds to the examination apparatus selection unit 1431.

In the ophthalmic information system of the embodiment, the data processor of the server may include a fee processor. The fee processor is configured to, when a charge occurs, calculate a fee for each of institutions including: any one or more of the medical institutions; one or more institutions where any one or more of the ophthalmic examination apparatuses are installed; and one or more system administering authorities, based on an amount to be charged and rules determined in advance. Here, the amount of the fee for any one or more of the institutions may be zero. With this configuration, fees can be automatically distributed to a plurality of users. Incidentally, in the above example, the fee processor corresponds to the accounting processor 170, and the rules correspond to the fee calculation rule 126.

The fee processor may be configured as follows. When a report is sent to a patient terminal, the fee processor calculates a fee for each of institutions including: the medical institution that has created the report; the institution where the ophthalmic examination apparatus, which has generated examination data used to create the report, is installed; and the system administering authority. With this configuration, fees for the examination and the generation of the report can be automatically distributed to users involved in those activities as a reward.

The ophthalmic information system of the embodiment may be configured as follows. First, the storage of the server includes a plurality of medical institution information storage areas respectively associated with a plurality of medical institution identification information corresponding to a plurality of medical institutions. When the fee processor has calculated the amount of fees, the third controller stores the amount of fee for the corresponding medical institution in a medical institution information storage area associated with the medical institution identification information of the corresponding medical institution. Incidentally, in the above example, the medical institution information storage area corresponds to the medical institution information storage area 122. With this configuration, the amount of fees for a plurality of medical institutions can be managed with respect to each of the medical institutions. Thus, the amount of fees for each medical institution can be suitably aggregated and notified to the medical institution.

The ophthalmic information system of the embodiment may be configured as follows. The server can communicate, via a communication line, with an insurance provider server that manages information related to each of one or more insurance providers. The storage of the server stores, in advance, second association information, in which each piece of patient identification information is associated with the insurance provider identification information of one or more of the insurance providers. When a charge occurs, the data processor specifies insurance provider identification information associated with the patient identification information of a patient related to the charge based on the second association information. Besides, the third controller controls the third communication unit to send the amount to be charged to the insurance provider server corresponding to the insurance provider identification information specified. With this configuration, when fees for a patient are charged to an insurance provider, the accounting process can be performed automatically. Incidentally, in the above example, the insurance provider server corresponds to the insurance provider server 800-h. The second association information is stored, for example, in the account (the patient information storage area 121) of each patient user. In another example, the second association information may be independent information in which information related to a plurality of patients (patient user IDs, etc.) and information related to a plurality of insurance providers (insurance provider user IDs, etc.) are associated with one another. In the above example, the process performed by the data processor for accounting corresponds to the accounting process of the accounting processor 170.

The ophthalmic information system of the embodiment may be configured as follows. The storage of the server may include one or more insurance provider information storage areas respectively associated with one or more insurance provider identification information corresponding to one or more insurance providers. In addition, the storage stores, in advance, second association information, in which each piece of patient identification information is associated with the insurance provider identification information of one or more of the insurance providers. When a charge occurs, the data processor specifies insurance provider identification information associated with the patient identification information of a patient related to the charge based on the second association information. The third controller stores the type and amount of the charge in one or more of the insurance provider information storage areas associated with the one or more pieces of insurance provider identification information specified. With this configuration, the amount of fees can be managed with respect to each of the insurance providers. Thus, the amount of fees for each insurance provider can be suitably aggregated and notified to the insurance provider. Incidentally, in the above example, the insurance provider information storage area corresponds to the insurance provider information storage area 125. The second association information is stored, for example, in the account (the patient information storage area 121) of each patient user. In another example, the second association information may be independent information in which information related to a plurality of patients (patient user IDs, etc.) and information related to a plurality of insurance providers (insurance provider user IDs, etc.) are associated with one another. In the above example, the process performed by the data processor for accounting corresponds to the accounting process of the accounting processor 170.

The ophthalmic examination apparatus may have an OCT function. In this case, the examination unit of the ophthalmic examination apparatus includes an optical system configured to perform OCT measurement, and an examination data generating unit. The optical system splits light emitted from a light source into measurement light and reference light. The optical system superposes the measurement light returning from a patient's eye on the reference light to generate interference light. The optical system detects the interference light. The examination data generating unit processes a detection result obtained by the optical system to thereby generate examination data. With this configuration, useful examination data can be obtained by utilizing the superiority of OCT (ability to acquire a high-resolution image, a cross-sectional image, and a three-dimensional image, and the like), and a report can be created based on it. Incidentally, in the above example, the optical system corresponds to the optical unit 210, and the examination data generating unit corresponds to the image forming unit 250 and the examination data generating unit 261.

[Ophthalmic Information Processing Server]

The ophthalmic information processing server of the embodiment can be operated as a server of the ophthalmic information system. The ophthalmic information processing server includes a communication unit, a storage, a data processor, and a controller.

The communication unit has a function to communicate with each of a plurality of ophthalmic examination apparatuses, each of a plurality of medical institution terminals, and each of a plurality of patient terminals via a communication line. Here, the ophthalmic apparatus is installed in a facility different from the medical institutions and, and generates examination data by optically examining the eye. The medical institution terminal is installed in the medical institution, and is used to create a report based on the examination data. The patient terminals are used by a plurality of patients or those related to the patients.

The storage includes a plurality of patient information storage areas respectively associated with a plurality of patient identification information corresponding to a plurality of patients. In addition, the storage stores, in advance, association information in which each patient identification information is associated with medical institution identification information of one or more of the plurality of medical institutions.

When the communication unit receives patient identification information and examination data from any of the ophthalmic examination apparatuses, the data processor specifies one or more medical institution terminals corresponding to the patient identification information from among the plurality of medical institution terminals with reference to the association information.

The controller is configured to control the communication unit to send the patient identification information and the examination data received by the communication unit to the medical institution terminal(s) specified by the data processor. When the communication unit receives patient identification information and a report from a medical institution terminal, the controller stores at least part of the report in one of the patient information storage areas associated with the patient identification information. The controller is further configured to control the communication unit to send at least part of the report to one of the patient terminals corresponding to the patient identification information.

With the ophthalmic information processing server having such a configuration, through the process related to the examination data of the eye acquired in a facility other than medical institutions such as a pharmacy, an optometrist, etc., and through the process relates to a report created by a doctor based on the examination data, the report can be provided to the patient. As a result, examination can be more readily carried out on a regular basis as compared to before for a disease that requires long-term pathology management.

The ophthalmic information processing server of the embodiment may be configured to be able to perform any one or more of the processes that can be implemented by the server of the ophthalmic information system described above.

The configurations described above are mere examples for embodying or carrying out the present invention, and therefore susceptible to several modifications and variations (omission, substitution, addition, etc.), all coming within the scope of the invention.

Any one or more of computer programs for realizing the above embodiments may be stored in an arbitrary recording medium that is readable by a computer. Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like.

The program(s) may be sent/received through a network such as the Internet, LAN, or the like.

The invention claimed is:

1. An ophthalmic information system, comprising:
a server;
a plurality of medical institution terminals installed in a plurality of medical institutions, each of the medical institution terminals being communicable with the server via a network;
a plurality of ophthalmic examination apparatuses, each of the ophthalmic examination apparatuses being communicable with the server via the network; and
a plurality of patient terminals used by a plurality of patients or those related to the patients, each of the patient terminals being communicable with the server via the network, wherein
each of the plurality of ophthalmic examination apparatuses is installed in a facility different from the plurality of medical institutions, each of the plurality of ophthalmic examination apparatuses including:
a first communication unit for communication via the network;
a receiving unit configured to receive patient identification information that identifies a patient;
an optical system for optically examining an eye and generating examination data based on results of the optical system optically examining the eye; and
a first controller configured to associate the patient identification information with the examination data, and to control the first communication unit to send the patient identification information and the examination data associated with each other to the server,
each of the plurality of medical institution terminals includes:
a second communication unit for communication via the network;
a user interface used to create a report based on the examination data; and
a second controller configured to control the second communication unit to send the report created to the server, and
the server includes:
a third communication unit for communication via the network, for receiving patient identification information and examination data from one ophthalmic examination apparatus of the plurality of ophthalmic examination apparatuses, and for receiving second patient identification information and a report from one medical institution terminal of the plurality of medical institution terminals;
a storage, including a plurality of patient information storage areas respectively associated with a plurality of patient identification information of the plurality of patients, that stores first association information that associates each of the plurality of patient identification information with medical institution identification information of one or more of the medical institutions;
a data processor configured to, when the third communication unit receives the patient identification information and the examination data from the one ophthalmic examination apparatus, specify a medical institution terminal corresponding to the patient identification information with reference to the first association information; and
a third controller configured to control the third communication unit to send the patient identification information and the examination data to the medical institution terminal specified by the data processor, wherein
the third controller is configured, when the third communication unit receives the second patient identification information and the report from the one medical institution terminal, to store at least part of the report in a patient information storage area associated with the second patient identification information, and to control the third communication unit to send the at least part of the report to a patient terminal corresponding to the second patient identification information,
the storage stores setting information corresponding to a particular patient identification information, the setting information indicating system specific settings of the optical system that are specific for the patient identified by the particular patient identification information,
the server sends the setting information to an ophthalmic examination apparatus corresponding to the particular patient identification information and the ophthalmic examination apparatus is set, according to the setting information, prior to the examination of the particular patient.

2. The ophthalmic information system according to claim 1, wherein
the data processor is configured to determine whether the report includes a visit request for a patient, and
the third controller is configured to perform different processes for a case where the report contains the visit request and a case where the report does not include the visit request.

3. The ophthalmic information system according to claim 2, wherein the third controller is configured to, when the report includes the visit request, control the third communication unit to send information to the patient terminal corresponding to the patient identification information, the information indicating a request to visit a medical institution corresponding to the medical institution identification information associated with the patient identification information in the first association information.

4. The ophthalmic information system according to claim 2, wherein the third controller is configured to store a determination result of the data processor in the patient information storage area associated with the patient identification information when the report includes the visit request.

5. The ophthalmic information system according to claim 1, wherein
the storage stores examination timing information indicating timing for conducting an examination,
the data processor is configured to select one or more of the plurality of patient terminals based on the examination timing information, and
the third controller is configured to control the third communication unit to send information requesting implementation of the examination to the one or more patient terminals selected by the data processor.

6. The ophthalmic information system according to claim 5, wherein
the examination timing information includes information indicating interval between examinations,
the third processor is configured to store, when the third communication unit receives patient identification information and examination data from one of the plurality of ophthalmic examination apparatuses, an examination data in the patient information storage area associated with the patient identification information, the examination date indicating a date on which the examination data is acquired, and the data processor is configured to select a patient terminal based on a most recent examination date stored in the patient information storage area, and the interval between examinations.

7. The ophthalmic information system according to claim 1, wherein the storage stores apparatus location information indicating a location of each of the plurality of ophthalmic examination apparatuses, the third controller is configured to store patient location information indicating a location of a patient in a corresponding patient information storage area, the data processor is configured to select one or more of the plurality of ophthalmic examination apparatuses based on the apparatus location information and the patient location information, and the third controller is configured to control the third communication unit to send information indicating the location of the ophthalmic examination apparatus selected by the data processor to a patient terminal corresponding to the patient.

8. The ophthalmic information system according to claim 1, wherein the data processor includes a fee processor configured to, when a charge occurs, calculate a fee for each of a plurality of institutions including one or more of the medical institutions, one or more institutions where one or more of the ophthalmic examination apparatuses are installed, and a system administering authority, based on an amount of the charge and rules determined in advance.

9. The ophthalmic information system according to claim 8, wherein the fee processor calculates, when the report is sent to one or more of the patient terminals, a fee for each of a plurality of institutions including a medical institution that has created the report, an institution where an ophthalmic examination apparatus, which has generated examination data used to create the report, is installed, and the system administering authority.

10. The ophthalmic information system according to claim 8, wherein the storage of the server includes a plurality of medical institution information storage areas respectively associated with a plurality of medical institution identification information corresponding to the plurality of medical institutions, and the third controller stores, when the fee processor has calculated an amount of the fee, the amount of the fee for a corresponding medical institution in a medical institution information storage area associated with the medical institution identification information of the corresponding medical institution.

11. The ophthalmic information system according to claim 8, wherein the server is communicable with an insurance provider server that manages information related to each of one or more insurance providers via the network, the storage stores second association information, in which each of the plurality of patient identification information is associated with insurance provider identification information of one or more of the insurance providers, the data processor is configured to specify, when a charge occurs, insurance provider identification information associated with patient identification information of a patient related to the charge based on the second association information, and the third controller is configured to control the third communication unit to send the amount of the charge to the insurance provider server corresponding to the insurance provider identification information specified.

12. The ophthalmic information system according to claim 8, wherein the storage includes one or more insurance provider information storage areas respectively associated with one or more insurance provider identification information corresponding to one or more insurance providers, and the storage storing second association information in which each of the plurality of patient identification information is associated with insurance provider identification information of one or more of the insurance providers, the data processor is configured to specify, when a charge occurs, insurance provider identification information associated with patient identification information of a patient related to the charge based on the second association information, and the third controller stores a type and an amount of the charge in the insurance provider information storage area associated with the insurance provider identification information specified.

13. The ophthalmic information system according to claim 1, wherein the optical system of each of the plurality of ophthalmic examination apparatuses is configured to split light emitted from a light source into measurement light and reference light, superpose the measurement light returning from a patient's eye on the reference light to generate interference light, and detect the interference light, and the optical system of each of the plurality of ophthalmic examination apparatus includes an examination data generating unit configured to process a detection result obtained by the optical system to generate the examination data.

14. An ophthalmic information processing server, comprising:

a communication unit for communication, via a network, with each of a plurality of ophthalmic examination apparatuses installed in a facility different from a plurality of medical institutions, each of the plurality of ophthalmic examination apparatuses including an optical system for optically examining an eye and generating examination data based on results of the optical system optically examining the eye, each of a plurality of medical institution terminals installed in the plurality of medical institutions to create a report based on the examination data, and each of a plurality of patient terminals used by a plurality of patients or those related to the patients;

a storage, including a plurality of patient information storage areas respectively associated with a plurality of patient identification information of the plurality of patients, that stores association information that associates each of the plurality of patient identification information with medical institution identification information of one or more of the medical institutions;

a data processor configured to, when the communication unit receives patient identification information and examination data from one ophthalmic examination apparatus of the plurality of ophthalmic examination apparatuses, specify a medical institution terminal corresponding to the patient identification information with reference to the association information; and a controller configured to control the communication unit to send the patient identification information and the examination data to the medical institution terminal specified by the data processor, wherein when the communication unit receives second patient identification information and a report from one of the plurality of medical institution terminals, the controller is further configured to store at least part of the report in a patient information storage area associated with the second patient identification information, and control the communication unit to send the at least part of the report to a patient terminal corresponding to the second patient identification information, the storage stores setting information corresponding to a particular patient identification information, the setting information indicating system specific settings of the optical system that are specific for the patient identified by the particular patient identification information, the server sends the setting information to an ophthalmic examination apparatus corresponding to the particular patient identification information and the ophthalmic examination apparatus is set, according to the setting information, prior to the examination of the particular patient.

\* \* \* \* \*